United States Patent
Trent et al.

(10) Patent No.: US 7,960,540 B2
(45) Date of Patent: Jun. 14, 2011

(54) ANTIPROLIFERATIVE ACTIVITY OF G-RICH OLIGONUCLEOTIDES AND METHOD OF USING SAME TO BIND TO NUCLEOLIN

(75) Inventors: John O. Trent, Louisville, KY (US); Paula J. Bates, Louisville, KY (US); Donald M. Miller, Louisville, KY (US)

(73) Assignee: Advanced Cancer Therapeutics, LLC, Louisville, KY (US)

( * ) Notice: Subject to any disclaimer, the term of this patent is extended or adjusted under 35 U.S.C. 154(b) by 69 days.

(21) Appl. No.: 11/982,427

(22) Filed: Oct. 31, 2007

(65) Prior Publication Data

US 2008/0318888 A1 Dec. 25, 2008

Related U.S. Application Data

(63) Continuation-in-part of application No. 09/958,251, filed as application No. PCT/US00/09311 on Apr. 7, 2000, now Pat. No. 7,314,926.

(60) Provisional application No. 60/128,316, filed on Apr. 8, 1999, provisional application No. 60/149,823, filed on Aug. 19, 1999.

(51) Int. Cl.
*C07H 21/00* (2006.01)
*C07H 21/02* (2006.01)

(52) U.S. Cl. .................. 536/24.5; 536/23.1; 536/24.3; 536/24.33

(58) Field of Classification Search .............. None
See application file for complete search history.

(56) References Cited

U.S. PATENT DOCUMENTS

| | | | |
|---|---|---|---|
| 4,141,359 A | 2/1979 | Jacobsen et al. | |
| 5,176,996 A | 1/1993 | Hogan et al. | |
| 5,262,409 A | 11/1993 | Margolis et al. | |
| 5,310,892 A | 5/1994 | Aris et al. | |
| 5,342,774 A | 8/1994 | Boon et al. | |
| 5,359,047 A | 10/1994 | Donahue et al. | |
| 5,416,202 A | 5/1995 | Bernhard et al. | |
| 5,432,070 A | 7/1995 | Schumacher et al. | |
| 5,443,962 A | 8/1995 | Draetta et al. | |
| 5,444,149 A | 8/1995 | Keene et al. | |
| 5,449,758 A | 9/1995 | Hartley | |
| 5,470,971 A | 11/1995 | Kondo et al. | |
| 5,489,508 A | 2/1996 | West et al. | |

(Continued)

FOREIGN PATENT DOCUMENTS

AU 775412 B2 7/2004

(Continued)

OTHER PUBLICATIONS

Benner et al. 1997, Journal of Pharmacological and Toxicological Methods vol. 37, Issue 4, Jun. 1997, pp. 229-235.*

(Continued)

*Primary Examiner* — Sean McGarry
*Assistant Examiner* — Terra Cotta Gibbs
(74) *Attorney, Agent, or Firm* — Hamilton, Brook, Smith & Reynolds, P.C.

(57) ABSTRACT

Compositions and methods for modulating tumor proliferation in an individual are provided. The methods employ nucleolin-binding agents, such as aptamers. The aptamers of the present invention can be used to modulate the proliferation of malignant, dysplastic, hyperproliferative, and/or metastatic cells through interference with molecular interactions and functions of nucleolin in the tumor cell.

11 Claims, 14 Drawing Sheets

U.S. PATENT DOCUMENTS

| | | |
|---|---|---|
| 5,494,818 A | 2/1996 | Baker et al. |
| 5,495,070 A | 2/1996 | John |
| 5,499,967 A | 3/1996 | Teillaud et al. |
| 5,523,389 A | 6/1996 | Ecker et al. |
| 5,561,222 A | 10/1996 | Keene et al. |
| 5,567,604 A | 10/1996 | Rando et al. |
| 5,582,981 A | 12/1996 | Toole et al. |
| 5,583,016 A | 12/1996 | Villeponteau et al. |
| 5,594,120 A | 1/1997 | Brenner et al. |
| 5,612,201 A | 3/1997 | De Plaen et al. |
| 5,614,503 A | 3/1997 | Chaudhary et al. |
| 5,624,799 A | 4/1997 | Kohwi-Shigematsu et al. |
| 5,624,818 A | 4/1997 | Eisemann et al. |
| 5,625,031 A | 4/1997 | Webster et al. |
| 5,631,146 A | 5/1997 | Szostak et al. |
| 5,643,778 A | 7/1997 | Nishikura |
| 5,643,890 A | 7/1997 | Iversen et al. |
| 5,645,986 A | 7/1997 | West et al. |
| 5,656,430 A | 8/1997 | Chirikjian et al. |
| 5,670,621 A | 9/1997 | Donahue et al. |
| 5,677,428 A | 10/1997 | Nishikura |
| 5,686,306 A | 11/1997 | West et al. |
| 5,688,511 A | 11/1997 | Gaynor et al. |
| 5,691,145 A | 11/1997 | Pitner et al. |
| 5,695,932 A | 12/1997 | West et al. |
| 5,705,334 A | 1/1998 | Lippard et al. |
| 5,707,795 A | 1/1998 | West et al. |
| 5,714,575 A | 2/1998 | Inouye et al. |
| 5,734,040 A | 3/1998 | Weeks et al. |
| 5,741,677 A | 4/1998 | Kozlowski et al. |
| 5,756,710 A | 5/1998 | Stein et al. |
| 5,763,174 A | 6/1998 | Nishikura |
| 5,763,178 A | 6/1998 | Chirikjian et al. |
| 5,776,696 A | 7/1998 | Salowe |
| 5,780,447 A | 7/1998 | Nienhuis |
| 5,780,610 A | 7/1998 | Collins et al. |
| 5,783,398 A | 7/1998 | Marcy et al. |
| 5,792,613 A | 8/1998 | Schmidt et al. |
| 5,804,380 A | 9/1998 | Harley et al. |
| 5,834,247 A | 11/1998 | Comb et al. |
| 5,837,453 A | 11/1998 | Harley et al. |
| 5,837,857 A | 11/1998 | Villeponteau et al. |
| 5,843,732 A | 12/1998 | Davis et al. |
| 5,849,564 A | 12/1998 | Chang et al. |
| 5,854,223 A | 12/1998 | Stein et al. |
| 5,861,498 A | 1/1999 | Alnemri et al. |
| 5,863,726 A | 1/1999 | Harley et al. |
| 5,866,680 A | 2/1999 | Keene et al. |
| 5,888,739 A | 3/1999 | Pitner et al. |
| 5,891,639 A | 4/1999 | Harley et al. |
| 5,925,729 A | 7/1999 | Boon et al. |
| 5,932,475 A | 8/1999 | Bandman et al. |
| 5,932,556 A | 8/1999 | Tam |
| 5,948,680 A | 9/1999 | Baker et al. |
| 5,952,490 A | 9/1999 | Hanecak et al. |
| 5,968,506 A | 10/1999 | Weinrich et al. |
| 5,972,692 A | 10/1999 | Hashimoto et al. |
| 5,985,320 A | 11/1999 | Edwards et al. |
| 5,989,823 A | 11/1999 | Jayasena et al. |
| 5,989,860 A | 11/1999 | Bandman et al. |
| 5,994,072 A | 11/1999 | Lam et al. |
| 6,013,639 A | 1/2000 | Peyman et al. |
| 6,017,536 A | 1/2000 | Barney et al. |
| 6,017,709 A | 1/2000 | Hardin et al. |
| 6,020,139 A | 2/2000 | Schwartz et al. |
| 6,025,194 A | 2/2000 | Funk |
| 6,025,474 A | 2/2000 | van den Eynde et al. |
| 6,027,881 A | 2/2000 | Paviakis et al. |
| 6,028,058 A | 2/2000 | Florkiewicz |
| 6,030,955 A | 2/2000 | Stein et al. |
| 6,036,955 A | 3/2000 | Thorpe et al. |
| 6,037,329 A | 3/2000 | Baird et al. |
| 6,054,265 A | 4/2000 | Barney et al. |
| 6,054,442 A | 4/2000 | Chen et al. |
| 6,057,423 A | 5/2000 | Brenner et al. |
| 6,060,065 A | 5/2000 | Barney et al. |
| 6,063,906 A | 5/2000 | Brenner et al. |
| 6,068,973 A | 5/2000 | Barney et al. |
| 6,071,732 A | 6/2000 | Moore |
| 6,080,727 A | 6/2000 | Zupi |
| 6,093,399 A | 7/2000 | Thorpe et al. |
| 6,093,794 A | 7/2000 | Barney et al. |
| 6,107,029 A | 8/2000 | Giordano |
| 6,121,434 A | 9/2000 | Peyman et al. |
| 6,126,965 A | 10/2000 | Kasid et al. |
| 6,127,173 A | 10/2000 | Eckstein et al. |
| 6,127,175 A | 10/2000 | Vigne et al. |
| 6,153,408 A | 11/2000 | Abastado et al. |
| 6,165,786 A | 12/2000 | Bennett et al. |
| 6,165,789 A | 12/2000 | Monia et al. |
| 6,166,178 A | 12/2000 | Cech et al. |
| 6,171,843 B1 | 1/2001 | Bandman et al. |
| 6,177,254 B1 | 1/2001 | Rattner et al. |
| 6,180,348 B1 | 1/2001 | Li |
| 6,183,751 B1 | 2/2001 | Chang et al. |
| 6,194,206 B1 | 2/2001 | West et al. |
| 6,200,746 B1 | 3/2001 | Fisher et al. |
| 6,214,805 B1 | 4/2001 | Torrence et al. |
| 6,228,983 B1 | 5/2001 | Barney et al. |
| 6,235,313 B1 | 5/2001 | Mathiowitz et al. |
| 6,235,525 B1 | 5/2001 | van den Eynde et al. |
| 6,251,585 B1 | 6/2001 | Draetta et al. |
| 6,255,055 B1 | 7/2001 | Ross |
| 6,261,556 B1 | 7/2001 | Weinrich et al. |
| 6,265,548 B1 | 7/2001 | Paviakis et al. |
| 6,274,313 B1 | 8/2001 | Weeks et al. |
| 6,274,725 B1 | 8/2001 | Sanghvi et al. |
| 6,288,042 B1 | 9/2001 | Rando et al. |
| 6,291,187 B1 | 9/2001 | Kingsmore et al. |
| 6,300,321 B1 | 10/2001 | Scherman et al. |
| 6,313,266 B1 | 11/2001 | Bandman et al. |
| 6,316,200 B1 | 11/2001 | Nadeau et al. |
| 6,320,039 B1 | 11/2001 | Villeponteau et al. |
| 6,323,185 B1 | 11/2001 | Rando et al. |
| 6,331,396 B1 | 12/2001 | Silverman et al. |
| 6,331,617 B1 | 12/2001 | Weeks et al. |
| 6,332,897 B1 | 12/2001 | Weiner et al. |
| 6,333,191 B1 | 12/2001 | Inouye et al. |
| 6,333,314 B1 | 12/2001 | Kasid et al. |
| 6,335,170 B1 | 1/2002 | Orntoft |
| 6,348,586 B1 | 2/2002 | Chang et al. |
| 6,355,785 B1 * | 3/2002 | Rando et al. .......... 536/23.1 |
| 6,365,187 B2 | 4/2002 | Mathiowitz et al. |
| 6,368,789 B1 | 4/2002 | West et al. |
| 6,376,226 B1 | 4/2002 | Alnemri |
| 6,379,888 B1 | 4/2002 | Nadeau et al. |
| 6,383,752 B1 | 5/2002 | Agrawal et al. |
| 6,399,302 B1 | 6/2002 | Lannigan et al. |
| 6,399,392 B1 | 6/2002 | Haugland et al. |
| 6,416,959 B1 | 7/2002 | Giuliano et al. |
| 6,420,122 B1 | 7/2002 | Housman et al. |
| 6,423,493 B1 | 7/2002 | Gorenstein et al. |
| 6,426,231 B1 | 7/2002 | Bayley et al. |
| 6,444,643 B1 | 9/2002 | Steiner et al. |
| 6,444,870 B1 | 9/2002 | Zhang et al. |
| 6,455,042 B1 | 9/2002 | Brenner et al. |
| 6,455,250 B1 | 9/2002 | Aguilera et al. |
| 6,465,176 B1 | 10/2002 | Giordano et al. |
| 6,475,789 B1 | 11/2002 | Cech et al. |
| 6,475,791 B1 | 11/2002 | Lippard et al. |
| 6,479,055 B1 | 11/2002 | Bolognesi et al. |
| 6,479,301 B1 | 11/2002 | Balch et al. |
| 6,630,480 B1 | 10/2003 | Gourdeau et al. |
| 7,314,926 B1 * | 1/2008 | Miller et al. .......... 536/24.1 |
| 7,357,928 B2 | 4/2008 | Bates et al. |
| 7,541,150 B2 | 6/2009 | Miller et al. |
| 2001/0041681 A1 | 11/2001 | Phillips et al. |
| 2004/0132049 A1 | 7/2004 | Bates et al. |
| 2005/0053607 A1 | 3/2005 | Bates et al. |
| 2008/0318887 A1 | 12/2008 | Trent et al. |
| 2008/0318888 A1 | 12/2008 | Trent et al. |
| 2008/0318889 A1 | 12/2008 | Trent et al. |
| 2008/0318890 A1 | 12/2008 | Trent et al. |
| 2009/0131351 A1 | 5/2009 | Green et al. |
| 2009/0326047 A1 | 12/2009 | Miller et al. |

FOREIGN PATENT DOCUMENTS

| | | |
|---|---|---|
| EP | 1181304 B1 | 10/2007 |
| JP | 11-346800 | 12/1999 |
| WO | WO 93/23572 | 11/1993 |
| WO | WO 94/08053 A1 | 4/1994 |
| WO | WO 99/07383 | 2/1999 |
| WO | WO 99/42113 | 8/1999 |
| WO | WO 00/61597 | 10/2000 |
| WO | WO 01/44465 | 6/2001 |
| WO | WO 03/086174 | 10/2003 |
| WO | WO 2004/003554 A1 | 1/2004 |
| WO | WO 2005/035579 | 4/2005 |
| WO | WO 2005/037323 | 4/2005 |
| WO | WO 2009/098464 | 8/2009 |

OTHER PUBLICATIONS

Miller, D., "Unique G-Rich Oligonucleotides Which Inhibit the Growth of Prostatic Carcinoma Cells," US DoD Award No. DAMDI7-98-1-8583, (Sep. 1999).

Cutts, S. M., et al., "A Gel Mobility Shift Assay for Probing the Effect of Drug-DNA Adducts on DNA-Binding Proteins," *Methods in Molecular Biology*, 90:95-106 (1997).

Agrawal et al., "Mixed Backbone Oligonucleotides: Improvement in Oligonucleotide-Induced Toxicity in Vivo," *Antisense & Nucleic Acid Drug Development* (1998) 8:135-139.

Barton et al., "Antisense oligonucleotides directed against p53 have antiproliferative effects unrelated to effects on p53 expression," *British Journal of Cancer* (1995) 71:429-437.

Benimetskaya et al., "Formation of a G-tetrad and higher order structures correlates with biological activity of the RelA (Nf-κB p65) 'antisense' oligodeoxynucleotide," *Nucleic Acids Research* (1997) 25(13):2648-2656.

Branch, "A good antisense molecule is hard to find," *Trends Biochem. Sci.* (1998) 23:45-50.

Chen et al., "Activity and Mechanism of Action of AS1411 in Acute Myeloid Leukemia Cells," *American Society of Hematology's 49th Annual Meeting*, Dec. 8-11, 2007.

Cleland et al., "Development of poly-(D,L,-lactide-coglycolide) microsphere formulations containing recombinant human vascular endothelial growth factor to promote local angiogenesis," *Journal of Controlled. Release* (2001) 72:13-24.

Cleland, "Protein Delivery from Biodegradable Microspheres," *Pharm. Biotechnol.* (1997) 10:1-43.

Crooke, "An Overview of Progress in Antisense Therapeutics," *Antisense & Nucleic Acid Drug Development* (1998) 8:115-122.

Dapic et al., "Antiproliferative Activity of G-Quartet-Forming Oligonucleotides with Backbone and Sugar Modifications," *Biochemistry* (2002) 41:3676-3685.

Derenzini et al., "The Quantity of Nucleolar Proteins Nucleolin and Protein B23 is Related to Cell Doubling Time in Human Cancer Cells," *Laboratory Investigation* (1995) 73(5):497-502.

Derossi et al., "Trojan peptides: the penetratin system for intracellular delivery," *Trends in Cell Biology* (1998) 8:84-87.

Dryden et al., "The lack of specificity of neuropeptide Y (NPY) antisense oligodeoxynucleotides administered intracerebroventricularly in inhibiting food intake and NPY gene expression in the rat hypothalamus," *Journal of Endocrinology* (1998) 157:169-175.

Fry et al., "The fragile X syndrome d(DGG)η nucleotide repeats form a stable tetrahelical structure," *Proc. Natl. Acad. Sci. USA* (1994) 91:4950-4954.

Gerwitz et al., "Nucleic Acid Therapeutics: State of the Art and Future Prospects," *Blood* (1998) 92(3):712-736.

Ginisty et al., "Nucleolin functions in the first step of ribosomal RNA processing," *The EMBO Journal* (1998) 17(5):1476-1486.

Ginisty et al., "Structure and functions of nucleolin," *Journal of Cell Science* (1999) 112:761-772.

Girvin et al., "AGRO100 inhibits activation of a nuclear factor-κB (NF- κB) by forming a complex with NF-κB essential modulator (NEMO) and nucleolin," *Mol. Cancer. Ther.* (2006) 5(7):1790-1799.

Gotzmann et al., "Two-dimensional electrophoresis reveals a nuclear matrix-associated nucleolin complex of basic isoelectric point," *Eletrophoresis* (1997) 18:2645-2653.

Hélène et al., "Sequence-specific control of gene expression by antigene and clamp oligonucleotides," *Ciba Found. Symp.* (1997) 209:94-106.

Ireson et al., "Discovery and development of anticancer aptamers," *Mol. Cancer Ther.* (2006) 5(12):2957-2962.

Kibbey et al., "A 110-kD Nuclear Shuttling Protein, Nucleolin, Binds to the Neurite-Promoting IKVAV Site of Laminin-1," *J. of Neuro. Res.* (1995) 42:314-322.

Lapeyre et al., "Nucleolin, the major nucleolar protein of growing eukaryotic cells: An unusual protein structure revealed by the nucleotide sequence," *Proc. Natl. Acad. Sci. USA* (1987) 84:1472-1476.

Lee et al., "The Nucleolin Binding Activity of Hepatitis Delta Antigen Is Associated with Nucleolus Targeting," *J. of Biolog. Chem.* (1998) 273(13):7650-7656.

Léger-Silvestre et al., "Ultrastructural changes in the *Schizosaccharomyces pombe* nucleolus following the disruption of the gar2+ gene, which encodes a nucleolar protein structurally related to nucleolin," *Chromosoma* (1997) 105:542-552.

Murchie et al., "Retinoblastoma susceptibility genes contain 5' sequences with a high propensity to form quanine-tetrad structures," *Nucleic Acids Research* (1992) 20(1):49-53.

Otake et al., "Overexpression of nucleolin in chronic lymphocytic leukemia cells induces stabilization of bcl2 mRNA," *Blood* (2007) 109(7):3069-3075.

Ritchie et al., "Combination of the aptamer AS1411 with paclitaxel or Ara-C produces synergistic inhibition of cancer cell growth," *ACCR Annual Meeting* 2007.

Roussel et al., "Identification of Ag-NOR Proteins, Markers of Proliferation Related to Ribosomal Gene Activity," *Exp. Cell Res.* (1994) 214:465-472.

Saijo et al., "Contiguous Four-guanosine Sequence in c-myc Antisense Phosphorothioate Oligonucleotides Inhibits Cell Growth on Human Lung Cancer Cells: Possible Involvement of Cell Adhesion Inhibition," *Jpn. J. Cancer Res.* (1997) 88:26-33.

Sen et al., "Formation of parallel four-stranded complexes by guanine-rich motifs in DNA and its implications for meiosis," *Nature* (1988) 334:364-366.

Shah et al., AS1411, a Novel DNA Aptamer as a Potential Treatment of Acute Myelogenous Leukaemia (AML), *American Society of Hematology 48th Annual Meeting*, Dec. 9-12, 2006.

Stein, "How to Design an Antisense Oligodeoxynucleotide Experiment: A Consensus Approach," *Antisense & Nucleic Acid Drug Development* (1998) 8:129-132.

Sundquist et al., "Evidence for interstrand quadruplex formation in the dimerization of human immunodeficiency virus I genomic RNA," *Proc. Natl. Acad. Sci. USA* (1993) 90:3393-3397.

Sundquist et al., "Telomeric DNA dimerizes by formation of guanine tetrads between hairpin loops," *Nature* (1989) 342:825-829.

Tuteja et al., "Human DNA helicase IV is nucleolin, an RNA helicase modulated by phosphorylation," *Gene* (1995) 160:143-148.

Tuteja et al., "Nucleolin: A Multifunctional Major Nucleolar Phosphoprotein," *Crit. Rev. Biochem. Mol. Biol.* (1998) 33(6):407-436.

Waggoner et al., "Viral Ribonucleoprotein Complex Formation and Nucleolar-Cytoplasmic Relocalization of Nucleolin in Poliovirus-Infected Cells," *J. Virol.* (1998) 72(8):6699-6709.

White et al., "Phosphorothioate-Capped Antisense Oligonucleotides to Ras GAP Inhibit Cell Proliferation and Trigger Apoptosis but Fail to Downregulate GAP Gene Expression," *Biochem. Biophys. Res. Commun.* (1996) 227:118-124.

Xu et al., "Inhibition of DNA Replication and Induction of S Phase Cell Cycle Arrest by G-rich Oligonucleotides," *J. Biol. Chem.* (2001) 276(46):43221-43230.

Yokoyama et al., "Synergy between Angiostatin and Endostatin: Inhibition of Ovarian Cancer Growth," *Cancer Research* (2000) 60(8):2190-2196.

Ratajczak, et al., "In Vivo Treatment in Human Leukemia in a SCID Mouse Model with C-MYB Antisense Oligodeoxynucleotides," *Proc. Natl. Acad. Sci. USA*, 89:11823-11827, (1992).

Sharma, et al., "Telomerase as a Potential Molecular Target to Study G-Quartet Phosphorothioates," *Antisense and Nucleic Acid Drug Development*, 6:3-7, (1996).

Ballou et al., "Three-Dimensional Imaging of Nucleolin Trafficking in Normal Cells, Transfectants, and Heterokaryons," *SPIE*, 2680:124-131, Apr. 1, 1996.

Bates et al., "Antiproliferative Activity of G-rich Oligonucleotides Correlates with Protein Binding," *Journal of Biological Chemistry* (1999) 274(37):26369-26377.

Burgess et al., "The antiproliferative activity of c-myb and c-myc antisense oligonucleotides in smooth muscle cells is caused by a nonantisense mechanism," *Proc. Natl. Acad. Sci. USA* (1995) 92:4051-4055.

Dapić et al., "Biophysical and biological properties of quadruplex oligodeoxyribonucleotides," *Nucl. Acids Res.* (2003) 31(8):2097-2107.

Dempsey, Laurie A., et al., "G4 DNA Binding by LR1 and Its Subunits, Nucleolin and hrRNP D, A Role for G-G pairing in Immunoglobulin Switch Recombination," *Journal of Biological Chemistry* (1999) 274(2):1066-1071.

Dermer, "Another Anniversary for the War on Cancer," *Bio/Technology* (1994) 12:320.

Gromeier et al., "Viruses for the treatment of malignant glioma," *Curr. Opin. Mol. Ther.* (2001) 3(5):503-508.

Gura, T., "Systems for Identifying New Drugs are Often Faulty," *Science* (1997) 278:1041-1042.

Ishikawa et al., "Nuclear Proteins That Bind the Pre-mRNA 3' Splice Site Sequence r(UUAGG/G) and the Human Telomeric DNA Sequence d(TTAGGG),,," *Molecular and Cellular Biology* (1993) 13(7):4301-4310.

Mata et al., "A Hexameric Phosphorothioate Oligonucleotide Telomerase Inhibitor Arrests Growth of Burkitt's Lymphoma Cells in Vitro and in Vivo," *Toxicology and Applied Pharmacology* (1997) 144:189-197.

Ohnuma et al., "Inhibitory Effects of Telomere-Mimic Phosphorothioate Oligonucleotides on Various Human Tumor Cells in Vitro," *Anticancer Research* (1997) 17:2455-2458.

Serin et al., "Two RNA-binding Domains Determine the RNA-binding Specificity of Nucleolin," *The Journal of Biological Chemistry* (1997) 272(20):13109-13116.

Weidner et al, "Phosphorothioate oligonucleotides bind in a non sequence-specific manner to the nucleolar protein C23/nucleolin," *FEBS Letters* (1995) 366:146-150.

Zendegui et al., "In vivo stability and kinetics of absorption and disposition of 3' phosphopropyl amine oligonucleotides," *Nucleic Acids Research* (1992) 20(2):307-314.

Advisory Action, U.S. Appl. No. 09/958,251, date of mailing, Sep. 8, 2006.

Advisory Action, U.S. Appl. No. 10/978,032, date of mailing, Oct. 9, 2009.

Advisory Action, U.S. Appl. No. 10/978,032, date of mailing, Jun. 24, 2008.

Alvarnas and Forman, "Graft Purging in Autologous Bone Marrow Transplantation: A Promise Not Quite Fulfilled," *Oncology*, 18(7):867-876 (2004).

Christian, et al., "Nucleolin Expressed at the Cell Surface is a Marker of Endothelial Cells in Angiogenic Blood Vessels," *J. Cell. Bio.*, 163(4):871-878 (2003).

Examiner Interview Summary, U.S. Appl. No. 10/978,032, date of mailing, Aug. 3, 2010.

Gribben, "The Alvarnas/Forman Article Reviewed," *Oncology*, 18(7):876 (2004).

Hanakahi, et al., "High Affinity Interactions of Nucleolin with G-G-Paired rDNA," *J. Biol. Chem.*, 274(22):15908-15912 (1999).

International Preliminary Examination Report for International Application No. PCT/US2000/09311, mailed Aug. 6, 2001.

Interview Summary, U.S. Appl. No. 09/958,251, date of mailing, Aug. 23, 2007.

Interview Summary, U.S. Appl. No. 09/958,251, date of mailing, Sep. 8, 2006.

Interview Summary, U.S. Appl. No. 10/978,032, date of mailing, Sep. 23, 2010.

Interview Summary, U.S. Appl. No. 10/978,032, date of mailing, May 6, 2009.

Interview Summary, U.S. Appl. No. 10/978,032, date of mailing, Apr. 11, 2008.

Interview Summary, U.S. Appl. No. 11/982,413, date of mailing, Sep. 23, 2010.

Ireson, et al., "Cancer Cell Kill, in Vivo Biodistribution and Anti-Tumor Properties of AS1411, a G-Rich Oligonucleotide Aptamer," Abstract No. 4713, Proc, Amer Assoc Cancer Research vol. 47, 2006.

Ireson, et al., "Preclinical Anticancer Properties of a G-Rich Oligonucleotide Based Aptamer AS1411.", Proc, Amer Assoc Cancer Research vol. 47, 2006.

Jayasena, "Aptamers: An Emerging Class of Molecules that Rival Antibodies in Diagnostics," *Clinical Chem.*, 45(9):1628-1650 (1999).

Johnson, et al., "Relationships Between Drug Activity in NCI Preclinical in Vitro and in Vivo Models and Early Clinical Trials," *Br. J. Cancer*, 18:84(10):1424-1431, May 2001.

Laber, et al., "A Phase I Study of AS1411 (AGRO100) in Advanced Cancer", Journal of Clinical Oncology, 2006 ASCO Annual Meeting, vol. 24, No. 18S.

Mergny, et al., "Following G-Quartet Formation by UV-Spectroscopy," *FEBS Letters*, 435:74-78 (1998).

Miller, et al., "Unique G-rich Oligonucleotides Which Inhibit the Growth of Prostatic Carcinoma Cells," US DOD Award No. DAMD17-98-1-8583 (Jul. 2003).

Mizutani, et al., "Enhancement of Sensitivity of Urinary Bladder Tumor Cells to Cisplatin by C-MYC Antisense Oligonucleotide," *Cancer* 74(9):2546-2554 (1994).

Nass, et al., "Defining a Role for Cmyc in Breast Tumorigenesis," *Breast Cancer Research Treatment*, 44:1-22 (1997).

Notice of Allowance, U.S. Application No. 09/958,251, date of mailing, Aug. 23, 2007.

Office Action, U.S. Appl. No. 09/958,251, date of mailing, Nov. 13, 2006.

Office Action, U.S. Appl. No. 09/958,251, date of mailing, Mar. 22, 2006.

Office Action, U.S. Appl. No. 09/958,251, date of mailing, Jul. 8, 2005.

Office Action, U.S. Appl. No. 10/978,032, date of mailing, Aug. 3, 2010.

Office Action, U.S. Appl. No. 10/978,032, date of mailing, May 29, 2009.

Office Action, U.S. Appl. No. 10/978,032, date of mailing, Oct. 30, 2008.

Office Action, U.S. Appl. No. 10/978,032, date of mailing, Jan. 28, 2008.

Office Action, U.S. Appl. No. 10/978,032, date of mailing, Apr. 24, 2007.

Porkka, et al., "A Fragment of the HMGN2 Protein Homes to the Nuclei of Tumor Cells and Tumor Endothelial Cells in Vivo," *Proc. Nat. Acad. Sci. USA*, 99(11):7444-49 (2002).

Vorhies and Nemunaitis, "Nucleic acid Aptamers for Targeting of shRNA-Based Cancer Therapeutics," *Biologics:Targets & Therapy*, 1(4):367-376 (2007).

White, et al., "Developing Aptamers into Therapeutics," *J. Clin. Invest.*, 106(8):929-934 (2000).

Williamson, "G-Quartets in Biology: Reprise," *Proc. Natl. Acad. Sci. USA*, 90:3124 (1993).

Written Opinion of International Searching Authority for International Application No. PCT/US2000/09311, date of mailing Apr. 17, 2001.

Bates, et al., "Discovery and Development of the G-Rich Oligonucleotide AS1411 as a Novel Treatment for Cancer," *Experimental and Molecular Pathology*, 86:151-164 (2009).

Carbone and Pass, "Multistep and Multifactorial Carcinogenesis: When does a contributing factor become a carcinogen?" *Seminars in Cancer Biology*, 14:399-405 (2004).

Eck and Wilson, "Goodman and Gilman's The Pharmacological Basis of Therapeutics," McGraw Hill, New York, pp. 77-101 (1996).

International Preliminary Report on Patentability, International Application No. PCT/GB2009/000326, date of mailing Aug. 19, 2010.

International Search Report, International Application No. PCT/GB2009/00326, date of mailing Nov. 23, 2009.

Keith, et al., Multicomponent Therapeutics for Networked Systems, *Nat. Rev. Drug Discovery*, 4(1):71-78 (2005).

Miller et al., "Extended Phase I Study of AS1411 in Renal and Non-Small Cell Lung Cancers," *Annals of Oncology*, 17(9), Abstract 450P (2006).

Ritchie, et al., "Combination of the Aptamer AS1411 with Paclitaxel or Ara-C Produces Synergistic Inhibition of Cancer Cell Growth," Poster ACCR Annual Meeting 2007.

Shah et al., "AS1411, a Novel DNA Aptamer as a Potential Treatment of Acute Myelogenous Leukaemia (AML)," Poster, American Society of Hematology 48th Annual Meeting (2006).

Shah, et al., AS1411, a Novel DNA Aptamer as a Potential Treatment of Acute Myelogenous Leukemia (AML), *Blood*, 108(11):564A65A (2006).

Written Opinion of the International Searching Authority, International Application No. PCT/GB2009/00326, date of mailing Aug. 5, 2010.

Office Action, U.S. Appl. No. 11/985,827, date of mailing Nov. 5, 2010.

Interview Summary, U.S. Appl. No. 11/985,827, date of mailing Sep. 7, 2010.

The International Search Report and Written Opinion of the International Searching Authority or the Declaration, International Application No. PCT/US2010/031768, date of mailing Oct. 8, 2010.

Ireson and Kelland, "Discovery and Development of Anticancer Aptamers," *Mol. Can. Ther.*, 5(12):2957-2962 (2006).

Xu, X., et al., "Inhibition of DNA Replication and Induction of S Phase Cell Cycle Arrest by G-rich Oligonucleotides," *J. Biol. Chem.*, 276(46):43221-43230 (2001).

An, J., et al., "VHL Expression in Renal Cell Carcinoma Sensitizes to Bortezomib (PS-341) through an NF-κB-dependent Mechanism," *Oncogene*, 24:1563-1570 (2005).

Turcotte, S., et al., "A Molecule Targeting VHL-Deficient Renal Cell Carcinoma that Induces Autophagy," *Cancer Cell*, 14:90-102 (2008).

Bates, P.J., et al., "Antiproliferative Activity of G-rich Oligonucleotides Correlates with Protein Binding," *J. Biol. Chem.*, 274(37):26369-26377 (1999).

Islam, A., et al., "Differential Response to AS1411 in a Pair of VHL-Positive and VHL-Negative Renal Carcinoma Cell Lines," *Proceedings of the American Association for Cancer Research Annual Meeting*, 51:1081 (2010).

US 6,020,459, 02/2000, Barney et al. (withdrawn)

\* cited by examiner

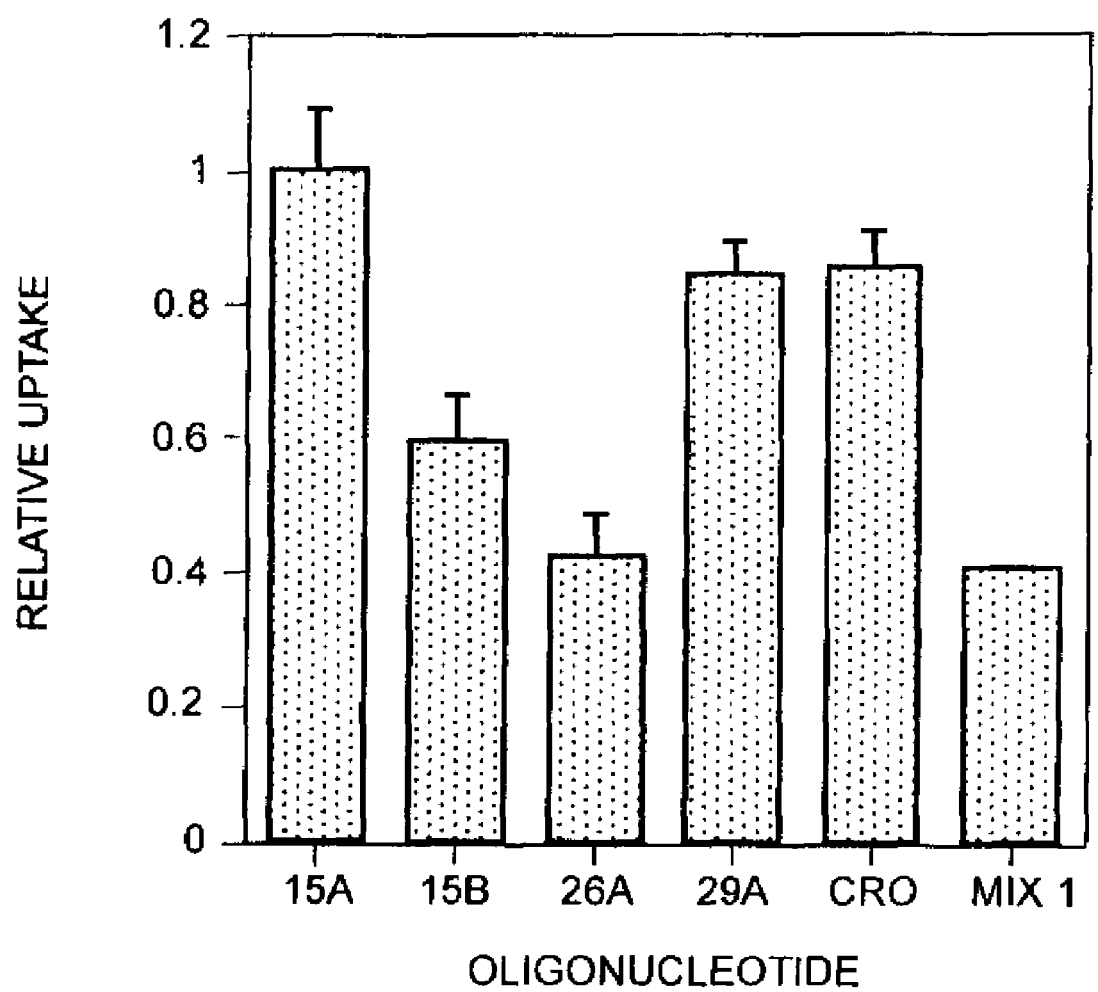

Key:
++, more than 95% growth inhibition
+, partial growth inhibition
N, no growth inhibition MDA is MDA-MB-231
MTX is a methotrexate resistant MCF-7 derivative

FIG - 10
GRO29A Treated Cells
(3 days after addition of GRO29A)
Untreated Cells
(in exponential growth phase)

15B: TTGGGGGGGGTGGGT (Inactive GRO)
29A: TTT(GGT)4TGT(GGT)3GG (Original GRO)
11A (T8): GGTGGTGGTGG
14C (D4): GGTGGTTGTGGTGG
26B (D8): (GGT)4TGT(GGT)3GG
32A (M4): (GGT)2TGT(GGT)2TGT(GGT)2TGTGGTGG
56A (M8): (GGT)4TGT(GGT)4TGT(GGT)4TGT(GGT)3GG

ANTIPROLIFERATIVE ACTIVITY OF G-RICH OLIGONUCLEOTIDES AND METHOD OF USING SAME TO BIND TO NUCLEOLIN

CROSS-REFERENCES TO RELATED APPLICATIONS

The present application is a continuation-in-part of U.S. patent application Ser. No. 09/958,251, filed Feb. 27, 2002, now U.S. Pat. No. 7,314,926, which application is a National Stage of International Application No. PCT/US00/09311, filed Apr. 7, 2000 and published as WO 00/61597, which application claims the benefit of U.S. Provisional Patent Application No. 60/128,316, filed Apr. 8, 1999, and the benefit of U.S. Provisional Patent Application No. 60/149,823, filed Aug. 19, 1999, the contents of each of which are incorporated herein by reference in their entirety for all purposes. The present application is related to U.S. patent application Ser. No. 10/978,032, filed on Oct. 29, 2004, the contents of which is incorporated herein by reference in its entirety for all purposes.

GOVERNMENT RIGHTS

This research was supported by the Department of Defense (CDMRP) Prostate Cancer Initiative Grant # DAMD-17-98-1-8583. The United States Government may have certain rights in this invention.

FIELD OF THE INVENTION

The present invention relates to tumor cell proliferation. More specifically, it relates to the use of nucleolin-binding agents to modulate tumor cell proliferation.

BACKGROUND OF THE INVENTION

In spite of numerous advances in medical research, cancer remains a leading cause of death throughout the developed world. Non-specific approaches to cancer management, such as surgery, radiotherapy and generalized chemotherapy, have been successful in the management of a selective group of circulating and slow-growing solid cancers. However, many solid tumors are considerably resistant to such approaches, and the prognosis in such cases is correspondingly grave.

Oligonucleotides have the potential to recognize unique sequences of DNA or RNA with a remarkable degree of specificity. For this reason they have been considered as promising candidates to realize gene specific therapies for the treatment of malignant, viral and inflammatory diseases. Two major strategies of oligonucleotide-mediated therapeutic intervention have been developed, namely, the antisense and antigene approaches.

The antisense strategy aims to down-regulate expression of a specific gene by hybridization of the oligonucleotide to the specific mRNA, resulting in modulation of translation. See Gewirtz el al. (1998) Blood 92, 712-736; Crooke (1998) Antisense Nucleic Acid Drug Dev. 8, 115-122; Branch (1998) Trends Biochem. Sci. 23, 45-50; Agrawal et al. (1998) Antisense Nucleic Acid Drug Dev. 8, 135-139. The antigene strategy, on the other hand, proposes to modulate transcription of a target gene by means of triple helix formation between the oligonucleotide and specific sequences in the double-stranded genomic DNA. See Helene el al. (1997) Ciba Found. Symp. 209, 94-102.

In addition to these two approaches, the use of aptamers holds great promise for therapeutic and diagnostic applications. Aptamers are oligonucleotides that can bind to a specific molecular partner through intramolecular or intermolecular interactions that fold the molecule into a complex tertiary structure. Such intramolecular or intermolecular structures allow aptamers to bind stably to their target molecules. See Osborne et al., 1997, Curr. Opin. Chem. Biol. 1:5-9; Patel, 1997, Curr. Opin. Chem. Biol. 1:32-46. Since nucleic acid molecules are typically more readily introduced into target cells than therapeutic protein molecules are, aptamers offer a method by which proliferative activity can be suppressed. Studies have shown that the administration of oligonucleotides can be administered in a clinically relevant way and have relatively few toxic side effects. See Gewirtz et al. (1998) Blood 92, 712-736; Agrawal et al. (1998) Antisense Nucleic Acid Drug Dev. 8, 135-139.

However, in spite of the approaches described above and those known in the art, curative measures effective against solid tumors and their cell proliferation have yet to be developed. As such, the development of agents that modulate hyperproliferative diseases and control tumor proliferation is of great medical and commercial importance.

SUMMARY OF THE INVENTION

The present invention provides a method for modulating the proliferation of malignant, dysplastic, and/or hyperproliferative cells in an individual by administering to the individual a therapeutically effective amount of a guanosine rich oligonucleotide.

The present invention also provides oligonucleotides which are capable of being specifically bound to a specific cellular protein which is implicated in the proliferation of cells, specifically malignant, dysplastic, and/or hyperproliferative cells.

The present invention also provides methods of screening for molecules or compounds capable of binding to G-rich oligonucleotide binding proteins.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIG. 5 is a chromatogram illustrating uptake of G-rich oligonucleotide by MDA-MB-231 breast cancer cells.

(B) Southwestern and Western blots of proteins captured from the lysates of MDA-MB-231 cells which had been treated with no oligonucleotide (none), active G-rich oligonucleotide (15A) or less active G-rich oligonucleotide (15B). (C) Southwestern and Western blots showing binding of GRO15A and nucleolin antibody to protein extracts (3 Rg/lane) from MDA-MB-231 cells: nuclear extracts (NU), cytoplasmic extracts (CY) and membrane proteins (ME).

FIG. 10 illustrates the results of immunofluoresence studies showing anti-nucleolin staining of MDA-MB-231 cells untreated (A) and treated (B) with GR029A 72 hours after treatment.

Figure 11:

FIG. 11: Staining of non-permeabilized DU145 cells with nucleolin antibody, showing the presence of nucleolin in the plasma membrane.

Figure 12C:
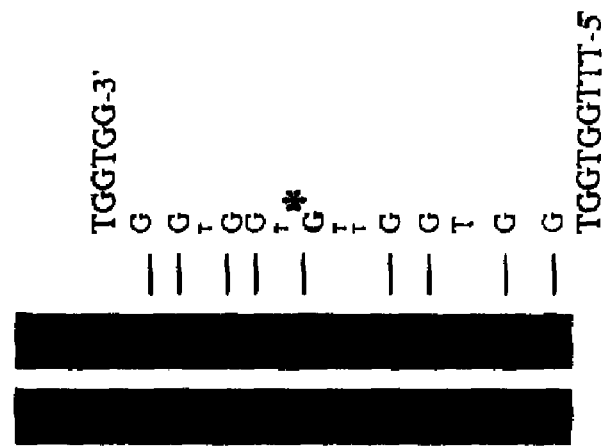
Figure 12B:
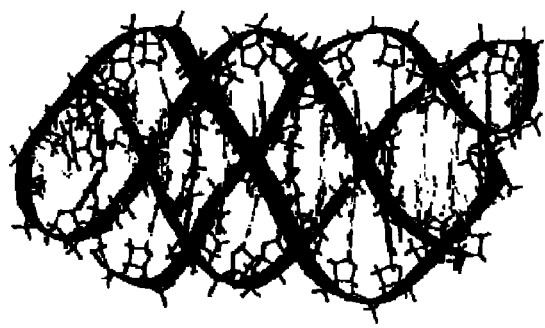
Figure 12A:
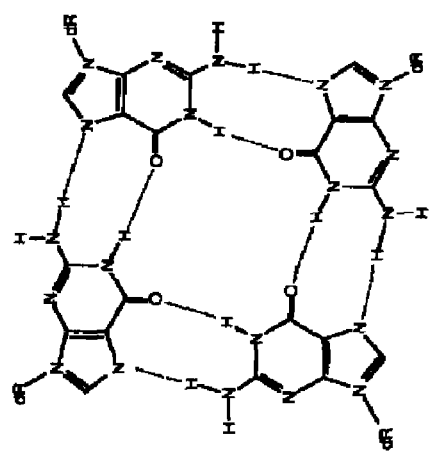

FIG. 12: (A) G-quartet, illustrating hydrogen bonding interaction.

(B) Molecular model of GR029A, showing a proposed dimeric structure stabilized by 8 G-quartets. (C) Dimethyl sulfate footprinting of GR029A, showing preferential methylation of the loop region guanosine, consistent with the predicted model.

Figures 13A, 13B:
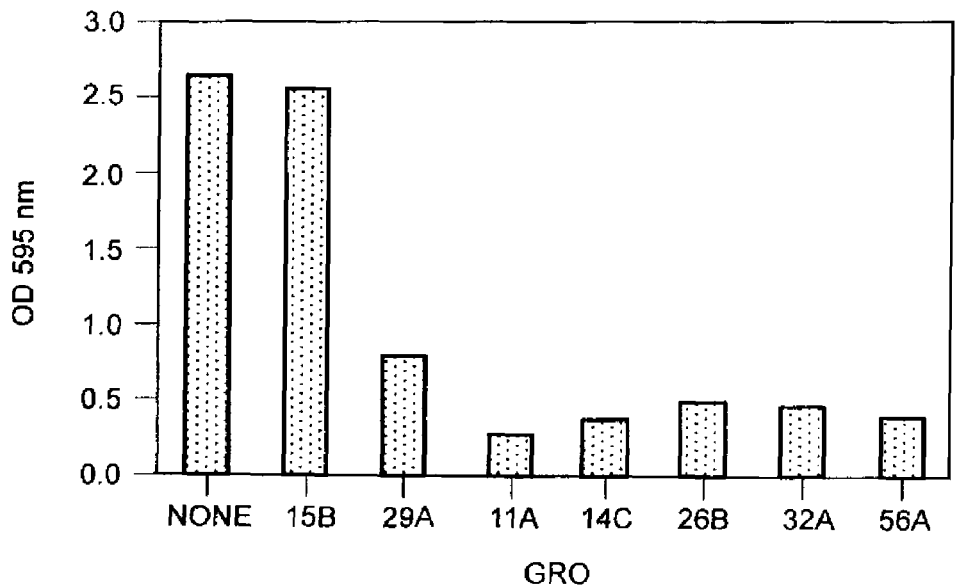

FIG. 13: (A) MTT assay showing antiprolilerative activity of novel guanosine-rich oligonucleotides against MDA-MB-231 breast cancer cells. (B) Sequences of novel guanosine-rich oligonucicotides.

Figure 14:
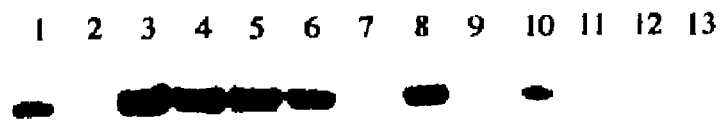
Figure 9A:
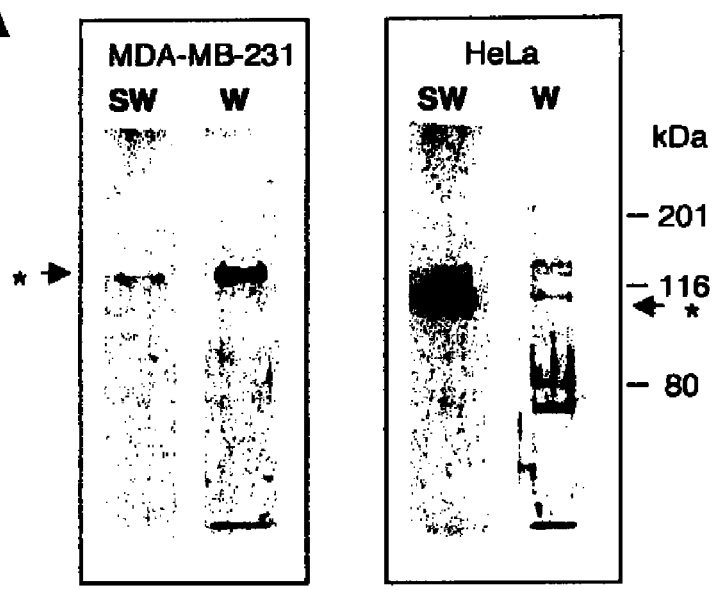
FIG. 9: (A) Southwestern (SW) and Western (W) blots probed respectively with 32P-labeled active G-rich oligonucleotide (GRO15A) or nucleolin antiserum Left panel shows MDA-MB-231 nuclear extracts (5 llg/lane); right panel shows HeLa nuclear extracts (Promega Inc., 5 <<ug/lane).
Figure 9B:
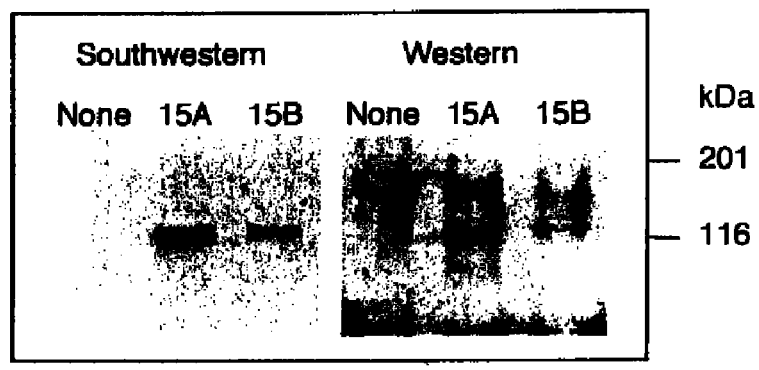
Figure 9C:
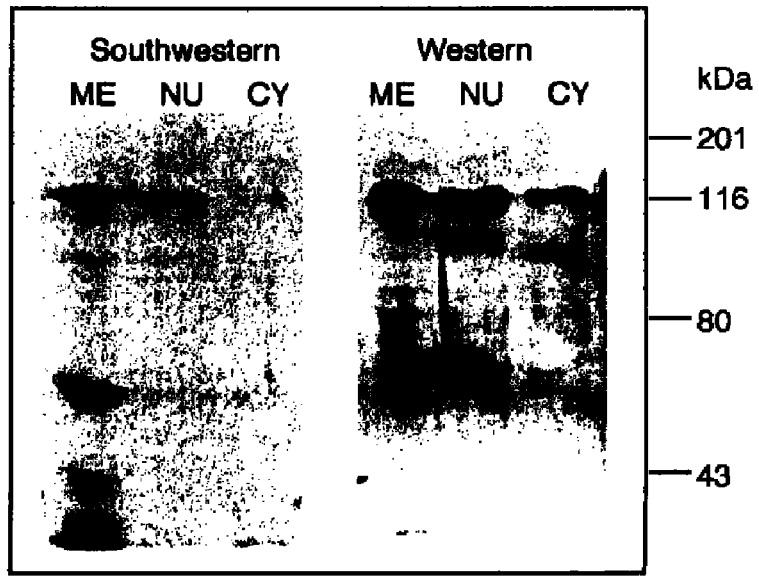

FIG. 14: A photograph depicting the results of an electrophoretic mobility shift assay for screening nucleolin-binding compounds wherein: Lane Description 1. GRO15B Inactive G-rich oligonucleotide 2. GR029A Antiproliferative G-rich oligonucleotide 3. Caffeine Stimulant; cAMP phosphodiesterase modulator 4.5-Fluorouracil Nucleoside analog; cancer drug; DNA damaging agent 5. Cisplatin Cancer drug; DNA crosslinker 6. Polymyxin B sulfate Polypeptide; antibiotic Lane Description 7. Ara-C Nucleotide analog; cancer drug; DNA damaging agent 8. Camptothecin Natural product; cancer drug; topoisomerase I modulateor 9. PMA Phorbol ester; tumor promoter; PKC activator 10. Taxol Natural product; cancer drug; anti-mitotic 11. Doxorubicin (adriamycin) Antitumor antibiotic; DNA binding agent 12. Heparin Polyanionic polysaccharide 13. OMR29A G-rich oligo with modified backbone; antiproliferative

DETAILED DESCRIPTION OF THE INVENTION

Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Hyperproliferative disorders: refers to excess cell proliferation, relative to that occurring with the same type of cell in the general population and/or the same type of cell obtained from a patient at an earlier time. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the individual's life. Hyperproliferative cell disorders can occur in different types of animals and in humans, and produce different physical manifestations depending upon the affected cells.

Hyperproliferative cell disorders include cancers. Cancers are of particular interest, including leukemias, lymphomas (Hodgkins and non-Hodgkins), and other myeloproliferative disorders; carcinomas of solid tissue, sarcomas, melanomas, adenomas, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like.

As used herein, the term "neoplastic" includes the new, abnormal growth of tissues and/or cells, such as a cancer or tumor, including, for example, breast cancer, leukemia or prostate cancer. The term "neoplastic" also includes malignant cells which can invade and destroy adjacent structures and/or metastasize.

As used herein, the term "dysplastic" includes any abnormal growth of cells, tissues, or structures including conditions such as psoriasis.

As used herein, the term "aptamer analog" or "analog of an aptamer" refers to a variant oligonucleotide, including RNA and DNA, wherein one or more residues of the reference aptamer has been substituted by other residue(s); wherein one or more residues, natural or synthetic, have been deleted from the reference aptamer sequence; and further includes aptamers having additional residues to the reference sequence and said variant oligonucleotide has a tertiary structure that can bind specifically to the same binding partner of the reference aptamer. The residues referred to above may be natural or modified/synthetically formed. Armed with the guidance of the present disclosure, those of ordinary skill in the art will be able to identify analogs using the systematic evolution of ligands by exponential enrichment (SELEX) process, which allows for the isolation of oligonucleotide sequences with the capacity to recognize virtually any class of target molecules with high affinity and specificity, and other technologies currently known in the art for identifying molecules having a certain binding specificity.

As used herein, the term "metastatic" or "metastatic disease" refers to diseases which have spread to regional lymph nodes or to distant sites and includes, without limitation, cancers and malignant tumors.

An individual "afflicted with" a particular disease means that the individual individual has been diagnosed as having, or is suspected as having, the disease.

The "individual;" or "patient," may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

As used herein, an "effective amount" (e.g., of an agent) is an amount (of the agent) that produces a desired and/or beneficial result. An effective amount can be administered in one or more administrations. For purposes of this invention, an effective amount is an amount sufficient to produce modulation of tumor cell proliferation. An "amount sufficient to modulate tumor cell proliferation" preferably is able to alter the rate of proliferation of tumor cells by at least 25%, preferably at least 50%, more preferably at least 75%, and even more preferably at least 90%.

Such modulation may have desirable concomitant effects, such as to palliate, ameliorate, stabilize, reverse, slow or delay progression of disease, delay or even prevent onset of disease.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds, such as plant or animal extracts, and the like. Agents include, but are not limited to, polyamine analogs. Agents can be administered alone or in various combinations.

"Modulating" cell proliferation means that the rate of proliferation is altered when compared to not administering an agent that interferes with nucleolin function (including, but not limited to, interfering with the cell cycle, arresting cell-cycle, for example at the S-phase, inhibiting DNA replication, inducing cell death, etc.), such as a nucleolin-binding aptamer. The mechanism of the present invention takes advantage of the presence of cell-surface nucleolin as a cancer marker. The binding of the modulating agents of the present invention brings about a cascade of events, including, but not limited to, uptake of the nucleolin-agent complex into the hyperproliferative cell and interference of nucleolin function in nucleus, cytoplasm and/or membrane. Preferably, "modulating" tumor cell proliferation means a change in the rate of tumor cell proliferation of at least 25%, preferably at least 50%, more preferably at least 75%, and even more preferably at least 90%. Generally, for purposes of this invention, "modulating" cell proliferation means that the rate of proliferation is decreased when compared to the rate of proliferation in that individual when no agent is administered. However, during the course of therapy, for example, it may be desirable to increase the rate of proliferation from a previously measured level. In individuals afflicted with tumors, the degree of modulation may be assessed by measurement of tumor cell proliferation, which will be discussed below, and generally entails detecting a proliferation marker(s) in a tumor cell population or uptake of certain substances which would provide a quantitative measure of proliferation. Any quantitative methods for measuring tumor cell proliferation currently known or unknown in the art can be used for this purpose. Further, it is possible that, if the cells are proliferating due to a genetic alteration (such as transposition, deletion, or insertion), this alteration could be detected using standard techniques in the art, such as RFLP (restriction fragment length polymorphism).

"Anti-proliferative agents," as used herein, refer to agents that modulate cell proliferation as defined herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 69087 amino acid sequence of SEQ ID NO: 2, 100 amino acid residues, preferably at least 200, 300, 400, or 500 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970, J. Mol. Biol. 48:444-453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2,3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989, CABIOS, 4:11-17) which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Autschul, et al. (1990, J. Mol. Biol. 215:403-410). BLAST nucleotide searches can be performed with the NBLAST program, score=100, wordlength=12 to obtain nucleotide sequences homologous to 69087, 15821, or 15418 nucleic acid molecules of the invention. BLAST protein searches can be performed with the XBLAST program, score=50, wordlength=3 to obtain amino acid sequences homologous to 69087, 15821, or 15418 protein molecules of the invention. To obtain gapped alignments for comparison purposes, gapped BLAST can be utilized as described in Altschul et al. al. (1997, Nucl. Acids Res. 25:3389-1 3402). When using BLAST and gapped BLAST programs, the default parameters of the respective programs (e.g., XBLAST and NBLAST) can be used. See <www.ncbi.nlm.nih.gov>.

The subject methods are used for prophylactic or therapeutic purposes. The term "treatment" as used herein refers to reducing or alleviating symptoms in an individual, preventing symptoms from worsening or progressing, modulation or elimination of the causative agent, or prevention of the disorder in an individual who is free therefrom. For example, treatment of a cancer patient may be reduction of tumor size, elimination of malignant cells, prevention of metastasis, or the prevention of relapse in a patient whose tumor has regressed. The treatment of ongoing disease, to stabilize or improve the clinical symptoms of the patient, is of particular interest. Such treatment is desirably performed prior to complete loss of function in the affected tissues.

Those skilled in the art are easily able to identify patients having a malignant, dysplastic, or a hyperproliferative condition such as a cancer or psoriasis, respectively. For example, patients who have a cancer such as breast cancer, prostate cancer, cervical carcinomas, and the like.

A "therapeutically effective amount" is an amount of an oligonucleotide of the present invention, that when administered to the individual, ameliorates a symptom of the disease, disorder, or condition, such as by modulating or reducing the proliferation of dysplastic, hyperproliferative, or malignant cells.

The present invention provides nucleolin-binding G-rich aptamers and methods of using same to modulate tumor cell proliferation. Nucleolin is a multifunctional 110 kDa phosphoprotein thought to be located predominantly in the nucleolus of proliferating cells (for reviews, see Tuteja el al. (1998) Crit. Rev. Biochem. Mol. Biol. 33, 407-436; Ginisty et al. (1999) J. Cell Sci. 112, 761-772). Nucleolin has been implicated in many aspects of ribosome biogenesis including the control of rDNA transcription, pre-ribosome packaging and organization of nucleolar chromatin. Tuteja et al. (1998) Crit. Rev. Biochem. Mol. Biol. 33, 407-436; Ginisty et al. (1999) J. Cell Sci. 112, 761-772; Ginisty et al. (1998) EMBO J. 17, 1476-1486.

Nucleolin is also implicated, directly or indirectly, in other roles including nuclear matrix structure (Gotzmann et al. (1997) Electrophoresis 18, 2645-2653), cytokinesis and nuclear division (Leger-Silvestre et al. (1997) Chromosoma 105, 542-52), and as an RNA and DNA helicase (Tuteja et al. (1995) Gene 160, 143-148). The multifunctional nature of nucleolin is reflected in its multidomain structure consisting of a histone-like N-terminus, a central domain containing RNA recognition motifs, and a glycine/arginine rich C-terminus. Lapeyre et al. (1987) Proc. Natl. Acad. Sci. U. S. A. 84, 1472-1476.

Levels of nucleolin are known to relate to the rate of cellular proliferation (Derenzini et al. (1995) Lab. Invest. 73, 497-502; Roussel et al. (1994) Exp. Cell Res. 214, 465-472.), being elevated in rapidly proliferating cells, such as malignant cells, and lower in more slowly dividing cells. For this reason, nucleolin is an attractive therapeutic target.

Although considered a predominantly nucleolar protein, the finding of nucleolin in the plasma membrane is consistent with several reports identifying cell surface nucleolin and suggesting its role as a cell surface receptor. Larrucea et al. (1998) J. Biol. Chem. 273, 31718-31725; Callebout et al. (1998) J. Biol. Chem. 273, 21988-21997; Semenkovich et al. (1990) Biochemistry 29, 9708; Jordan et al. (1994) Biochemistry 33, 14696-14706.

The synthesis of nucleolin is positively correlated with increased rates of cell division, and nucleolin levels are therefore higher in tumor cells as compared to most normal cells. In fact, nucleolin is one of the nuclear organizer region (NOR) proteins whose levels, as measured by silver staining, are assessed by pathologists as a marker of cell proliferation and an indicator of malignancy. Nucleolin is thus a tumor-selective target for therapeutic intervention, and strategies to reduce the levels of functional nucleolin are expected to modulate tumor cell growth.

The present invention provides novel guanine rich oligonucleotides (GROs) and methods of using at least one GRO to modulate the growth of neoplastic, dysplastic, hyperproliferative, and/or tumor cells in an individual.

Exemplary oligonucleotides of the present invention are designated below:

```
GRO14A                                      SEQ ID No: 1
5'-GTTGTTTGGGGTGG-3'

GRO15A                                      SEQ ID No: 2
5'-GTTGTTTGG GGTGGT-3'

GR025A                                      SEQ ID No: 3
5'-GGTTGGGGTGGGTGGGGTG GGTGGG-3'

GR028A                                      SEQ ID No: 4
5'-TTTGGTGGTGGTGGTTGTGG TGGTGGTG-3'

GR029A                                      SEQ ID No: 5
5'-TTTGGTGGTGGTGG TTGTGGTGGTGGTGG-3'

GR029-2                                     SEQ ID No: 6
5'-TTTGGTGG TGGTGGTTTTGGTGGTGGTGG-3'

GR029-3                                     SEQ ID No: 7
5'-TTTGGTGGTGGTGGTGGTGGTGGTGGTGG-3'

GR029-5                                     SEQ ID No: 8
5'-TTTGGTGGTGGTGGTTTGGGTGGTGG TGG-3'

GR029-13                                    SEQ ID No: 9
5'-TGGTGGTGGTGGT-3'

GRO11A                                      SEQ ID No: 10
5'-GGTGGTGGTGG-3'

GRO14C                                      SEQ ID No: 11
5'-GGTGGTTGTGGTGG-3'

GR026B                                      SEQ ID No: 12
5'-GGTGGTGGTGGTTGTGGTGG TGGTGG-3'

GR056A                                      SEQ ID No: 13
5'-GGTGGTGGTGGTTGTGGTGGTGGTGGTTGTGGTGGTGGTTGTGG
TGGTGG-3'

GR032A                                      SEQ ID No: 14
5'-GGTGGTTGTGGTGGTTGTGGTGGTTGT GGTGG-3'

GR032B                                      SEQ ID No: 15
5'-TTTGGTGGTGGTGGTTGTGGT GGTGGTGGTTT-3'

GR029-6                                     SEQ ID No: 16
5'-GGTGGTGGTGGTTGT GGTGGTGGTGGTTT-3'

GR028B                                      SEQ ID No: 17
5'-TTTGGTGGTGGT GGTGTGGTGGTGGTGG-3'

GRO13A                                      SEQ ID No: 18
5'-TGGTGGTGGT-3'
```

In a preferred embodiment, the aptamers of the invention has one or more of the following characteristics: (1) it modulates nucleolin function in the membrane; (2) it modulates nucleolin function in the cytosol; (3) it modulates nucleolin function in the nucleus; (4) it binds to nucleolin; (5) it modulates progression of a cell through the cell cycle; (6) it arrests cell cycle at the S-phase; (7) it induces nucleolin-mediated uptake into a cell; (8) it induces cell death; (9) it modulates gene transcription; (10) it has a molecular weight, amino acid composition or other physical characteristic of any of the aptamers of SEQ ID NO: 1-18, and 20; (11) it has an overall sequence identity of at least about 75%, preferably at least about 80%, more preferably about 85%, 86%, 87%, 88%, 89%, 90%, 91%, 92%, 93%, 94%, 95%, 96%, 97%, 98%, or 99% or more, with a portion of any of SEQ ID NO: 1-18 and 20; and (12) it has a nucleolin-binding domain which is preferably at least about 75%, preferably at least about 80%, more preferably about 85%, 86%, 87%, 88%, 89%, 90%, 91%, 92%, 93%, 94%, 95%, 96%, 97%, 98%, or 99% or more, with that of SEQ ID NO: 1-18 and 20; (13) it has a contiguous sequence identity of at least about 75%, preferably at least about 80%, more preferably about 85%, 86%, 87%, 88%, 89%, 90%, 91%, 92%, 93%, 94%, 95%, 96%, 97%, 98%, or 99% or more, with a portion of any of SEQ ID NO: 1-18 and 20.

Figure 3:
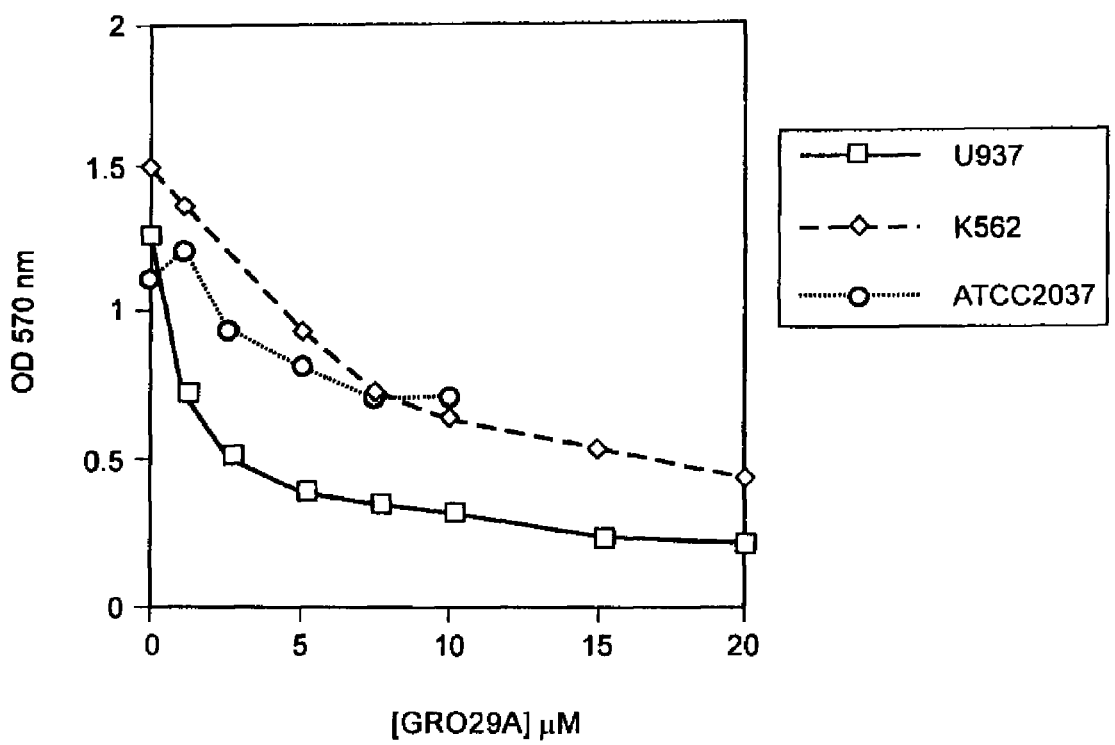
FIG. 3: MTT assays showing the dose dependence of growth modulation by GRO29A for leukemic cell lines, U937 and K563, and a non-malignant mouse hematopoietic stem cell line (ATCC 2037).

To provide just some examples of the effectiveness of the present invention, aptamers GR029-2, GR029-3, GR029-5, GR029-13, GRO15C, GR028H and GR0241 have been shown to modulate the growth of breast cancer cells and/or to compete for binding to the G-rich oligonucleotide binding protein as shown by an electrophoretic mobility shift assay (see FIG. 6 and 7). Demonstration of activity and protein binding of GROs of the present invention include GRO15A, 29A are shown in FIG. 1 and FIG. 6; GRO14A, 25A, 28A are shown in FIG. 7; GRO11A, 14C, 26B, 32A, 56A are shown in FIG. 3; GR029-2, 29-3,29-5,29-6,28B have demonstrated antiproliferative activity and protein binding. As will be detailed in the Example section, the present invention has also demonstrated effectiveness in modulating renal and non-small cell lung tumor cell proliferation in human clinical trials. In clinical study covering a broader range of tumor types, including NSCLC, lymphoma, renal, unknown (abdominal), gastric, colon, cervical, melanoma, prostate, pancreatic, hemangiopericytoma, pancreatic, and sarcoma (synovial), the present invention induced SD response in about 41% of the individuals and about 6% had a partial response and sustained near-complete response after over 10 months.

By G-rich oligonucleotide (GRO) it is meant that the oligonucleotides consist of 4-100 nucleotides (preferably 10-30 nucleotides) with DNA, RNA, 2'-O-methyl, phosphorothioate or other chemically similar backbones. Their sequences contain one or more GGT motifs. The oligonucleotides have antiproliferative activity against cells and bind to GRO binding protein and/or nucleolin. These properties can be demonstrated using the MTT assay and the EMSA technique shown in FIG. 6B, or other similar assays.

The oligonucleotides of the present invention are rich in guanosine and are capable of forming G-quartet structures. Specifically, the oligonucleotides of the present invention are primarily comprised of thymidine and guanosine with at least one contiguous guanosine repeat in the sequence of each oligonucleotide. The G-rich oligonucleotides are stable and can remain undegraded in serum for prolonged periods of time and have been found to retain their growth modulating effects for periods of at least seven days.

The GROs of the present invention can be administered to a patient or individual either alone or as part of a pharmaceutical composition. The GROs can be administered to patients either orally, rectally, parenterally (intravenously, intramuscularly, or subcutaneously), intracisternally, intravaginally, intraperitonally, intravesically, locally (powders, ointments, or drops), or as a buccal or nasal spray.

Pharmaceutical Formulations

The agents of the present invention can be incorporated into a variety of formulations for therapeutic administration. More than one of the agents described herein can be delivered simultaneously, or within a short period of time, by the same or by different routes. In one embodiment of the invention, a co-formulation is used, where the two components are combined in a single suspension. Alternatively, the two may be separately formulated.

The present invention also encompasses methods for modulating the proliferation of tumor cells and cells demonstrating malignant, dysplastic, hyperproliferative, or metastatic activity in an individual, comprising systemically (generally, orally) administering to a subject having a nervous system, particularly a vertebrate, preferably a mammal, most preferably a human, successive therapeutically effective doses of the present compositions.

In accordance with the methods of the present invention, the composition described herein is administered to a mammal, preferably a human. Preferably, such administration is oral. As used herein, the term "oral administration" (or the like) with respect to the subject (preferably, human) means that the subject ingests or is directed to ingest (preferably, for the purpose of treatment of one or more of the various health problems described herein) one or more components of the present invention/compositions of the present invention. Wherein the subject is directed to ingest one or more of the components of the present invention/compositions, such direction may be that which instructs and/or informs the user that use of the composition may and/or will provide treatment for the particular health problem of concern. For example, such direction may be oral direction (e.g., through oral instruction from, for example, a physician, sales professional or organization, and/or radio or television media (i.e., advertisement) or written direction (e.g., through written direction from, for example, a physician or other medical professional (e.g., scripts), sales professional or organization (e.g., through, for example, marketing brochures, pamphlets, or other instructive paraphernalia), written media (e.g., internet, electronic ma il, or other computer-related media), and/or packaging associated with the composition (e.g., a label present on a package containing the composition). As used herein, "written" means through words, pictures, symbols, and/or other visible descriptors.

Administration of the present components of the invention/compositions may be via any systemic method, however, such administration is preferably oral. Exemplary modes of administration include oral, rectal, topical, sublingual, transdermal, intravenous infusion, pulmonary, intramuscular, intracavity, aerosol, aural (e.g., via eardrops), intranasal, inhalation, needleless injection, or subcutaneous delivery. Direct injection could also be preferred for local delivery. For continuous infusion, a PCA device may be employed. Oral or subcutaneous administration may be important for the convenience of the patient as well as the dosing schedule. Preferred rectal modes of delivery include administration as a suppository or enema wash. For transdermal administration, an ionopheresis device may be employed to enhance penetration of the active drug through the skin. Such devices and methods useful in ionophoresis current assisted transdermal administration include those described in U.S. Pat. Nos. 4,141,359; 5,499,967; and 6, In some embodiments, partial doses or doses of different agents described herein are administered simultaneously or at different times by different routes. Such administration may use any route that results in systemic absorption, by any one of several known routes, including but not limited to inhalation, i.e. pulmonary aerosol administration; intranasal; sublingually; orally; and by injection, e.g. subcutaneously, intramuscularly, etc.

More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the therapeutic agent is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with each compound in the host.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Compositions of the present invention suitable for parenteral injection may comprise physiologically acceptable sterile aqueous or nonaqueous solutions, dispersions, suspensions or emulsions, and sterile powders for reconstitution into sterile injectable solutions or dispersions known in the art.

In some preferred embodiments, the compositions of the invention are administered intravenously, e.g. through attachment to a drip or infusion bag and any other similar means known in the art.

Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound (GRO) is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner.

Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a GRO of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

In addition, the GROs of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover GROs made either using standard organic synthetic techniques, including combinatorial chemistry or by biological methods, such as through metabolism.

Dosage

Generally, the GROs of the present invention can be given in single and/or multiple dosages or administered continuously. Depending on the patient and condition being treated and on the administration route, the agent(s) of the invention can be administered in dosages of about 1-100 mg/kg per day, preferably about 10-60 mg/kg, more preferably about 1-40 mg/kg, and even more preferably about 20-40 mg/kg or about 5-10 mg/kg. Administration can occur over a period ranging from about 1-10 days, preferably 1-7 days, and more preferably about 4-7 days. Those of ordinary skill in the art will appreciate that the mode of administration can have a large effect on dosage. Thus for example oral dosages maybe ten times the injection dose. The dosage for the anti-proliferative agents will also vary with the precise compound, in accordance with the nature of the agent. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the individual to side effects. Some of the specific compounds are more potent than others. Preferred dosages for a given compound are readily determinable by those of skill in the art by a variety of means. A preferred means is to measure the physiological potency of a given compound.

Susceptible Tumors

Tumors of interest include carcinomas, e.g. colon, prostate, breast, melanoma, ductal, endometrial, stomach, dysplastic oral mucosa, invasive oral cancer, non-small cell lung carcinoma, renal cell carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, and other myeloproliferative disorders, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Another cancer of interest is renal cell carcinoma. Renal cell carcinoma is the most common type of kidney cancer and accounts for more than 90% of malignant kidney tumors. Although renal cell carcinoma usually grows as a single mass within the kidney, a kidney may contain more than 1 tumor. Sometimes tumors may be found in both kidneys at the same time. Some renal cell carcinomas are noticed only after they have become quite large; most are found before they metastasize (spread) to other organs through the bloodstream or lymph vessels. Like most cancers, renal cell carcinoma is difficult to treat once it has metastasized. There are 5 main types of renal cell carcinoma: clear cell, papillary, chromophobe, collecting duct, and "unclassified."

Viewed under a microscope, the individual cells that make up clear cell renal cell carcinoma appear pale or clear. Papillary renal cell carcinoma generally forms little finger-like projections (called papillae) in some, if not most, of the tumor. The cells of chromophobe renal carcinoma also pale, like the clear cells, but are much larger and have certain other features that can be recognized. The fourth type, collecting duct renal carcinoma, is very rare and can be distinguished by the formation of irregular tubes. About 5% of renal cancers are unclassified because their appearance doesn't fit into any of the other categories.

Combination Therapy

The G-rich oligonucleotides in vitro of the present invention may also be used in combination with other chemotherapeutic agents to provide a synergistic or enhanced efficacy or modulation of neoplastic cell growth. For example, the G-rich oligonucleotides of the present invention can be administered in combination with chemotherapeutic agents including, without limitation, cis-platin, mitoxantrone, etoposide, camptothecin, 5-fluorouracil, vinblastine, paclitaxel, docetaxel, mithramycin A, dexamethasone, caffeine, and other chemotherapeutic agents well known to those skilled in the art. Experiments have shown that GRO29A acts synergistically with cis-platin in modulating MDA-MB-231 cell growth in vitro. Under conditions in which GRO29A has little effect by itself (5% growth modulation), a combination of cis-platin (0.5 pg/ml) and GR029A synergistically modulateed cell growth (63% modulation as compared to 29% modulation for cis-platin alone).

Methods for Selecting Nucleolin-Binding Oligonucleotides

Additionally, the present invention provides a method for selecting oligonucleotides that bind to nucleolin. The method utilizes an electrophoretic mobility shift assay (EMSA), as described below, to screen for oligonucleotides that bind strongly to nucleolin and which, therefore, would be expected, according to the present invention, to have antiproliferative activity. Oligonucleotides to be screened as potential antiproliferative agents are labeled and then incubated with nuclear extracts in the absence or presence of unlabeled competitor oligonucleotide and are allowed to react. The reaction mixtures are then electrophoresed and mobility shifts and/or bond intensity can be used to identify those oligonucleotides which have bound to the specific protein.

Figure 6A:
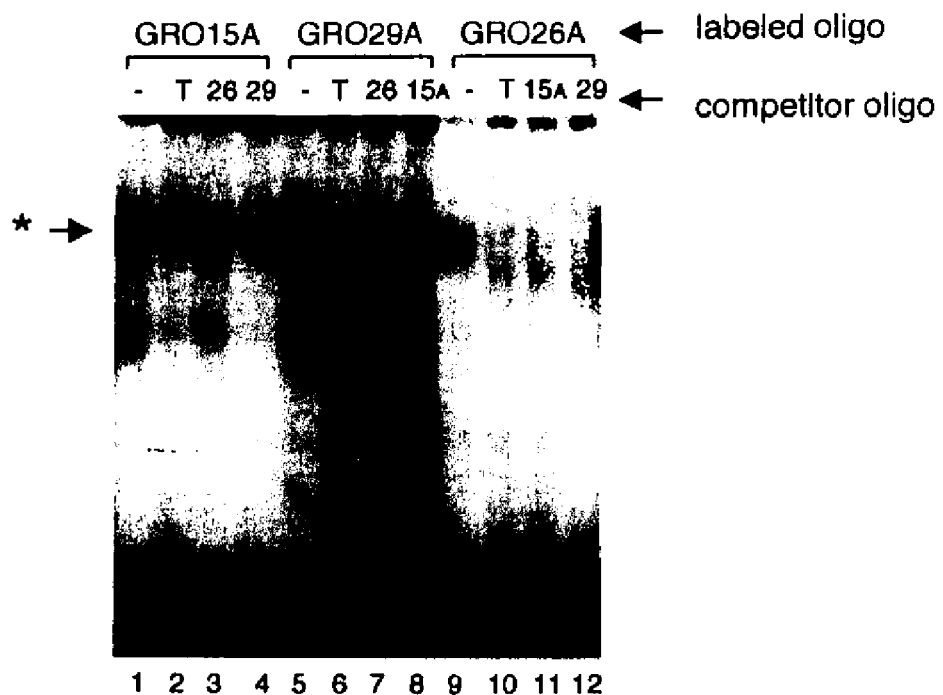
FIG. 6: (A) Electrophoretic mobility shift assay (EMSA) showing binding of 32P-labeled oligonucleotides to 5 u. g HeLa nuclear extracts and competition by unlabeled competitor oligonucleotides (100-fold molar excess over labeled oligonucleotide). Competitor oligonucleotides are abbreviated to T (TEL), 29 (GR029A), 26 (GR026A) and 15A (GR015A). (B) EMSA showing complexes formed between 32P-labeled TEL oligonucleotide (1 nM) and 5 ug HeLa nuclear extracts, and the effect of unlabeled competitor G-rich oligonucleotides (10 or 100 nM). (C) SDS-polyacrylamide gel showing complexes formed by UV crosslinking of labeled oligonucleotides and HeLa nuclear extracts incubated in the absence or presence of unlabeled competitor (100-fold molar excess). (D) Southwestern blot of HeLa nuclear extracts probed with 32P-labeled G-rich oligonucleotides ($2\times 10^6$ counts per min, approximately 0.75 nmol).
Figure 6B:
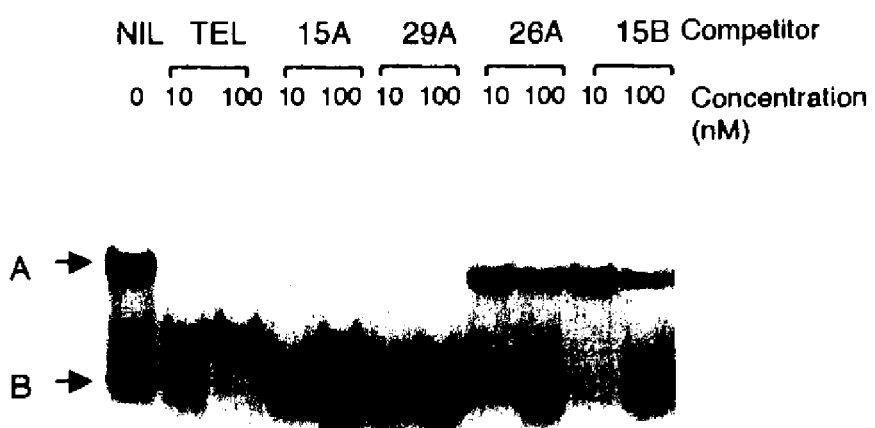

Alternatively, unlabeled compounds to be screened are incubated with nuclear extracts in the presence of labeled oligonucleotide (for example 5'-TTAGGGTTAGGG TTAGGG TTAGGG) and binding is assessed by a decrease in the intensity of the shifted band, as in FIG. 6B.

Alternatively, compounds to be screened can be added to cells growing in culture. Potential antiproliferative agents will be identified as those which cause an altered intensity and localization of nucleolin, as detected by immunofluorescence microscopy, as shown in FIG. 10.

Armed with the guidance of the present disclosure, those of ordinary skill in the art can also identify analogs using the systematic evolution of ligands by exponential enrichment (SELEX) process or any molecular modeling methods known in the art, which allow for the isolation of oligonucleotide sequences with the capacity to recognize virtually any class of target molecules with high affinity and specificity, and other technologies currently known in the art for identifying molecules having a certain binding specificity.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Oligonucleotides

3'-modified oligonucleotides were purchased from Oligos Etc. (Wilsonville, Oreg.) or synthesized at the University of Alabama at Birmingham using 3'-C3-amine CPG columns from Glen Research (Sterling, Va.). Unmodified oligonucleotides were obtained from Life Technologies, Inc., Gaithersburg, Md. Oligonucleotides were resuspended in water, precipitated in n-butyl alcohol, washed with 70% ethanol, dried and resuspended in sterile water or phosphate buffered saline (PBS). They were then sterilized by filtration through a 0.2 um filter. Each oligonucleotide was checked for integrity by 5'-radiolabeling followed by polyacrylamide gel electrophoresis (PAGE). The results reported in this paper were reproducible and independent of the source of synthetic oligonucleotides.

Cell Growth Assays

Cells were plated at low density (102 to 103 cells per well, depending on cell line) in the appropriate serum-supplemented medium in 96-well plates (one plate per MTT assay time point) and grown under standard conditions of cell culture. The following day (day 1) oligonucleotide, or water as control, was added to the culture medium to give a final concentration of 15 uM. Further oligonucleotide, equivalent to half the initial dose, was added to the culture medium on days two, three and four.

Cells were assayed using the MTT assay (Morgan (1998) Methods. Mol. Biol. 79, 179-183) on days one, three, five, seven and nine after plating. The culture medium was not changed throughout the duration of the experiment (which was the time required for untreated cells to grow to confluence). Experiments were performed in triplicate and bars represent the standard error of the data.

Figure 7A:
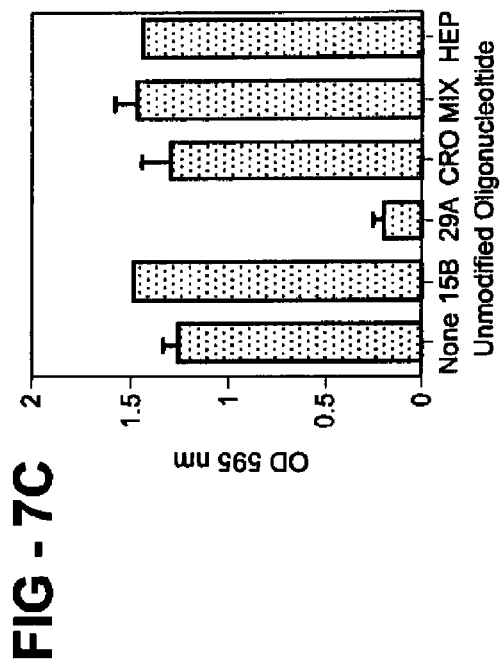
FIG. 7: (A) is a chromatogram illustrating an MTT assay of MDA-MB-231 cells treated with a single 10 uM dose of G-rich oligonucleotide or PBS as a control, the assay was performed on day 9 (oligonucleotide added on day 1); (B) illustrates an EMSA showing complex formed by binding of 5 pg of MDA-MB-231 nuclear extracts to 32P-labeled TEL oligonucleotide and competition by unlabeled G-rich oligonucleotides (10-fold molar excess); (C) is a chromatogram illustrating the results of a MTT assay of MDA-MB-231 cells treated with a single 10 RM dose of 3'-protected C-rich oligonucleotide (CRO) or mixed sequence oligonucleotide (MIX I) or with 20 units/ml heparin (HEP), in comparison with inactive (GRO15B) and active (GR029A) G-rich oligonucleotides wherein the assay was performed on day 7; and (D) is a chromatogram illustrating the results of an MTT assay of MDA-MB-231 cells treated with a single 10 uM dose of unmodified mixed sequence oligonucleotides, in comparison with an unmodified GRO29A analog (29A-OH) and TEL wherein to treat the cells, the culture medium was replaced by serum-free medium containing 10 uM oligonucleotide and after four hours at 37° C., fetal calf serum was added to give 10% v/v and the assay was performed on day 7.

For the experiment shown in FIG. 7A, MDA-MB-231 breast cancer cells (5×102 cells per well) were plated in a 96-well plate. After twenty-four hours, a single dose of oligonucleotide, or equal volume of PBS as a control, was added to the culture medium to a final concentration of 10 uM. Viable cells were assessed seven days after plating using the MTT assay. For the experiment using 3'-unmodified oligonucleotides (FIG. 7D), serum-supplemented medium was replaced by serum-free medium containing oligonucleotide (or serum-free medium alone in control wells). After incubation at 37° C. for four hours, fetal calf serum (Life Technologies, Inc.) was added to the medium to give 10% v/v.

Heparin used in these experiments was USP grade sodium salt derived from porcine intestine, purchased from Apothecon (Bristol-Myers Squibb Co.).

Working solutions were diluted from the stock (1000 units/ml) in sterile PBS.

Detection of G-Quartets by UV Spectroscopy

Oligonucleotides were resuspended in Tm buffer (20 mM Tris HCl, pH 8.0,140 mM KCl, 2.5 mM MgCl2) at a concentration such that A260=0.6 (molar concentrations ranged from 2.0 to 3.9 lem). Samples were annealed by boiling for five minutes and allowing to cool slowly to room temperature and overnight incubation at 4° C.

Thermal denaturation/renaturation experiments were carried out using an Amersham Pharmacia Biotech Ultrospec 2000 instrument equipped with a Peltier effect heated cuvette holder and temperature controller (Amersham Pharmacia Biotech). Absorbance at 295 nm was monitored over a temperature range of 25-95 or 20-90° C. at a heating/cooling rate of 0.5° C./min.

Oligonucleotide Uptake

MDA-MB-231 cells were seeded in twenty-four well plates at a density of 5×105 cells/well. After twenty-four hours, oligonuclebtide (5 nmol of unlabeled oligonucleotide and 5×106 cpm (approximately 1 pmol) of 5'-32P-labeled oligonucleotide) was added directly to the culture medium to give a final concentration of 10 pM. Cells were incubated at 37° C. for ten or twenty-six hours and were then washed three times with PBS. Cells were removed from the plate by trypsinization, washed, and collected in 100 ul of PBS. A 50-1 lu aliquot was counted by scintillation counting to assess cell-associated radioactivity. To ensure that the washing procedures were sufficient to remove all excess oligonucleotide, the final PBS wash was counted and found to be very low compared with the cell-associated radioactivity. The remaining 50-pl aliquots were boiled for five minutes and placed on ice. An equal volume of phenol/chloroform was added, and the oligonucleotides were extracted in the aqueous phase, precipitated with n-butyl alcohol, and analyzed by denaturing polyacrylamide gel electrophoresis on a 15% gel.

Electrophoretic Mobility Shift Assays (EMSAs)

Oligonucleotides were 5'-labeled with 32p using T4 kinase. Labeled oligonucleotide (final concentration 1 nM, approximately 50,000 cpm) was preincubated for thirty minutes at 37° C. either alone or in the presence of unlabeled competitor oligonucleotide. Nuclear extracts were added, and the sample was incubated a further thirty minutes at 37° C. Both the preincubation and binding reactions were carried out in Buffer A (20 mM Tris. HCl pH 7.4, 140 mM KCl, 2.5 mM MgCl2, 1 mM dithiothreitol, 0.2 mM phenylmethyl sulfonyl fluoride and 8% (v/v) glycerol). Electrophoresis was carried out using 5% polyacrylamide gels in TBE buffer (90 mM Tris borate, 2 mM EDTA).

UV Cross Linking

For the UV crosslinking experiments, samples were incubated as described above (EMSA). They were then placed on ice and irradiated at 5 cm from the source using the "autocross link" function of a Stratagene UV Stratalinker. Following irradiation, samples were electrophoresed under denaturing conditions on a 8% polyacrylamide-SDS gel using a standard Tris glycine buffer and visualized by autoradiography.

Southwestern Blotting

Nuclear extracts were electrophoresed on a 8% polyacrylamide-SDS gel and transferred to polyvinylidene difluoride (PVDF) membrane by electroblotting using a Tris glycine/methanol (10% v/v) buffer. Immobilized proteins were denatured and renatured by washing for thirty minutes at 4° C. with 6 M guanidine. HCl followed by washes in 1:1, 1:2 and 1:4 dilutions of 6M guanidine in HEPES binding buffer (25 mM HEPES pH 7.9, 4 mM KCl, 3 mM MgCl2). The membrane was blocked by washing for one hour in a 5% solution of non-fat dried milk (NDM) in binding buffer.

Hybridization of the labeled oligonucleotide (1-4×106 cpm) took place for two hours at 4° C. in HEPES binding buffer supplemented with 0.25% NDM, 0.05% Nonidet P 40,400 llg/ml salmon sperm DNA and 100 Fg/ml of an unrelated, mixed sequence 35-mer oligonucleotide (5'-TC- GAGAAAAACTCTCCTCTC CTTCCTTCCTCTCCA-3'SEQ ID No: 1.9). Membranes were washed in binding buffer and visualized by autoradiography.

Western Blotting

Western blotting was carried out at room temperature in PBS buffer containing Tween 20 at 0.1% (for polyclonal antibody) or 0.05% (monoclonal antibody). PVDF membranes were blocked with PBS-Tween 20 containing 5% NDM for one hour, washed and incubated for one hour with a 1:1000 dilution of nucleolin antiserum or nucleolin monoclonal antibody (MBL Ltd., Japan, 1 J. g/ml final concentration) in PBS-Tween 20. The membranes were washed three times for five minutes each wash in PBS/Tween 20 and incubated for one hour with secondary antibody diluted in PBS/Tween 20 (1:1000 anti-rabbit IgG-HRP or 1:2000 anti-mouse IgG-HRP). After washing the blot was visualized using ECL reagent (Amersham Pharmacia Biotech) according to the manufacturer's instructions.

Capture of Biotinylated Oligonucleotide-Protein Complexes

MDA-MB-231 cells were grown to 50% confluence in 90 mm dishes. 5'-Biotinylated oligonucleotides were added to the culture medium at a final concentration of 5 uM. After incubation for two hours at 37° C., cells were washed extensively with PBS and lysed by addition of 1 ml of lysis buffer (50 mM Tris. HCl pH 8.0, 150 mM NaCl, 0.02% (w/v) sodium azide, 0.1 mg/ml phenylmethyl sulfonyl fluoride, 1% (v/v) Nonidet P40, 0.5% (w/v) sodium deoxycholate, 0.5 mM dithiothreitol, 1 Fg/ml aprotinin) followed by incubation at −20° C. for ten minutes. Genomic DNA was sheared by repeated injection of the lysate through a fine gauge needle. Lysate was added to streptavidin coated magnetic beads (MagneSphere, Promega Inc.) and incubated ten minutes at room temperature. Beads were captured and unbound sample was removed. Beads were then washed twice with 1 ml of lysis buffer and again with 1 ml of Buffer A. Finally, proteins were eluted by addition of 50 ul of loading buffer (containing 1% SDS and 5% 2-mercaptoethanol) and incubation for fifteen minutes at 65° C.

Preparation of Nuclear, Cytoplasmic and Membrane Protein Extracts

HeLa nuclear extracts used in EMSAs were purchased from Promega Inc. (bandshift grade). Nuclear and cytoplasmic extracts from MDA-MB-231 cells were prepared using the protocol described in F. M. Ausubel et al. Ausubel et al. (Eds.) (1996) Current Protocols in Molecular Biology, Wiley, NY, Section 12.1. Plasma membrane proteins were prepared from MDA-MB-231 cells using a method previously described. Yao et al. (1996) Biochemical Pharmacology 51, 431-436; Naito et al. (1988) J. Biol. Chem. 263, 11887-11891.

India Ink Staining

The membrane was incubated for 15 minutes at room temperature in PBS-Tween 20 containing three drops of Higgins India Ink 4415 and washed with distilled water.

Nucleolin Binding Assay

To determine which non-oligonucleotide-based molecules or compounds are capable of binding to nucleolin, an EMSA was performed as described below and the results of which are shown in FIG. 14. In this assay, the binding ability of several different molecules or compounds for nucleolin was examined. This type of assay can be utilized to screen for molecules or compounds capable of binding nucleolin. As previously stated, those of ordinary skill in the art may employ conventional molecular modeling methods and/or SELEX to screen for other anti-proliferative agents, nucleolin-binding GROs, or aptamers.

Nuclear proteins (2.5 Rg, in this case from HeLa cells) were added to 5'-32P-labeled TEL oligonucleotide (5'-TTAGGGTTAGGGTTAGGGTTAGGG SEQ ID No: 20, 2 nM final concentration). Unlabeled competitor oligonucleotide or compound was added to give a final concentration of 50 nM oligonucleotide (equivalent to approximately 0.5 llg/ml for GRO29A) or 0.5 llg/ml (lanes 3-12). Binding reactions took place for 30 minutes at 37° C. in a buffer containing 20 mM Tris. HCl pH 7.4, 140 mM KCl, 2.5 mM MgCl2, 8% (v/v) glycerol, 1 mM DTT, 0.2 mM PMSF). Samples were analyzed on a 5% polyacrylamide gel using TBE buffer.

Chemotherapeutic Agent and GRO Experimental Protocol

Cisplatin (in 1% DMSO solution to give a final concentration of 0.5 pLg/ml) was added to the medium of MDA-MB-231 breast cancer cells growing in culture. After two hours, GRO29A (in PBS solution to give a final concentration of 8 uM) was added to the medium. After six days, the relative number of viable cells was determined using the MTT assay. Cells treated with GR029A alone received an appropriate volume of 1% DMSO in place of cisplatin. Cells treated with cisplatin alone received an appropriate volume of PBS in place of GR029A.

In vivo Efficacy of GROs Against Cancer

The following protocol can be used to demonstrate in vivo efficacy of GROs against prostate cancer and illustrate nucleolin levels and characteristics in prostate cells. As previously stated, nucleolin, which is involved in multiple aspects of cell division, i.e. proliferation, is the target for modulation in the present invention. Nucleolin levels (in the nucleus) bear a positive correlation with the rate of cell proliferation, and thus, strategies that modulate nucleolin have significant therapeutic potential.

Since levels of cell surface nucleolin are typically elevated in malignant cells relative to normal cells, nucleolin also poses as a useful tumor cell marker.

Determining the Activity of GROs in Normal and Malignant Prostate Tissue Cell Lines Nucleolin levels in the nucleus, cytoplasm and plasma membrane of these cells are examined using blotting techniques and immunofluorescence microscopy. Tumor uptake of GROs delivered by different methods in mouse and rat models of prostate cancer are also studied.

To study in vivo efficacy, nude mice with subcutaneous or orthotopically implanted tumor xenografts and the Dunning rat model of prostate cancer are used. Preliminary data indicated that GROs' synergistic effect with certain chemotherapy drugs. Therefore, the effects of combinations of GROs with a variety of cytotoxic and other agents in cultured cells are examined, and tested for any synergistic combinations in animal models. Finally, a homology model of nucleolin based on the reported structures of many similar proteins is constructed and used to identify potential small molecule modulators of nucleolin by a "virtual screening" method.

Conventional chemotherapy agents have been ineffective in prolonging survival in randomized trials of patients with hormone refractory prostate cancer, and novel therapeutic approaches are urgently required. The GROs of the present invention demonstrated strong modulatory effect against prostate cancer cells. They have a novel mechanism of action and enormous therapeutic potential in the fight against prostate cancer.

Testing of Oligonucleotide GR029A

Sensitivity of Various Malignant and Transformed Prostate Cell Lines, and the Relationship Between Sensitivity and Nucleolin/GRO Binding Protein Levels. The GIso value for GR029A against a variety of cell lines derived from human and rat prostate using the MTT assay was calculated.

These included hormone-dependent (LNCaP) and independent (DU145, PC-3), non-malignant (PZ-HPV-7 and rat YPEN-1), and multidrug resistant (rat AT3 B 1 and MLLB-2) cell lines, which are commercially available from ATCC and other sources employed by those of ordinary skill in the art.

To determine nucleolin levels, nuclear, cytoplasmic and plasma membrane extracts were prepared from each cell line by standard methods. See Bates et al. (1999) J. Biol. Chem. 274 (37): 26369-77. Extracts were electrophoresed on 8% polyacrylamide-SDS gels and transferred to PVDF membranes. They were examined by Southwestern blotting (with radiolabeled GRO) and Western blotting (with nucleolin monoclonal antibody, Santa Cruz) to determine levels of GRO-binding protein/nucleolin. Cells were also examined by immunofluorescent staining using nucleolin antibody under appropriate for staining either intracellular or cell surface proteins.

Optimization of Delivery of Oligonucleotides to Tumor Cells in Culture and In vivo.

To investigate the uptake of GR029A in cultured cells, a 5'-FITC labeled analog of GR029A is used. Cells (initially DU145 and PC-3) are treated with this oligonucleotide delivered by a variety of different methods, selected from the following: electroporation, cationic lipids (1 ag GR029A: 4 ug DOTAP-DOPE [1:1]), polymyxin B sulfate (Sigma), lactic acid nanoparticles (a simple synthesis is described in Berton et al. (1999) Eur. J. Pharm. Biopharm. 47 (2): 119-23), and streptolysin O permeabilization (Giles et al. (1998) Nucleic Acids Res. 26 (7): 1567-75).

Oligonucleotide uptake and intracellular localization are assessed by fluorescence microscopy. The effects of different delivery methods on the antiproliferative activity of GR029A are determined by the MTT assay. To determine whether the uptake characteristics of GR029A were significantly different from non-G-rich oligonucleotides, a comparison of the unassisted uptake of GR029A with C-rich and mixed sequence FITC-labeled oligonucleotides is made. If uptake is significantly different, investigation of the possibility that different receptors are utilized is carried out in experiments in which FITC labeled oligonucleotides are incubated with cells in the presence of unlabeled competitor oligonucleotides. These experiments provide important information regarding the uptake of oligonucleotides in general, and the importance of GRO interaction with nucleolin at the cell surface.

To examine the pharmacokinetics, stability and tumor delivery in vivo methods similar to those reported previously for a G-rich, phosphodiester oligonucleotide that is being evaluated as an anti-HIV agent are used. Wallace et al. (1997) J. Pharmacol. Exp. Ther. 280 (3): 1480-8. First, an analog of GR029A is synthesized that was internally labeled with 32p. This procedure has been described previously (Bishop et al. (1996) J. Biol. Chem. 271 (10): 5698-703), and involves the synthesis of two short oligonucleotide fragments, 5'-labeling of one fragment using T4 kinase, followed by template-directed ligation of the two fragments by T4 ligase.

The labeled oligonucleotide is then purified by polyacrylamide gel electrophoresis (PAGE). Male nude mice (nine in total) are subcutaneously (s.c.) inoculated by their hind flank with DU145 prostate cancer cells under mild anesthesia. When tumors are established (approximately 0.5 cm diameter), the mice are treated with a single 5 mg/kg dose of GR029A (a mixture of labeled and unlabeled oligonucleotide) in a volume of 25 u.l by intratumoral, intraperitoneal or intravenous (tail vein) injection. The animals are observed for evidence of acute toxicity and weight loss. On days two, four and seven after GRO injection, mice are euthanized by C02 inhalation, the tumor excised, and blood and organs collected. Levels of radioactivity in the tumor, serum, liver, kidney, spleen and prostate are examined. Stability was determined by denaturing PAGE of serum samples.

Similar experiments are also carried out using the Dunning prostatic carcinoma model. Isaacs et al. (1978) Cancer Res. 38 (11 Pt 2): 4353-9; Zaccheo et al. (1998) Prostate 35 (4): 237-42. These experiments help determine the optimal administration routes in rats and mice, and provide an indication of the optimal dosing schedule. All animal experiments strictly adhere to institutional guidelines on animal care and use.

Evaluation of the Efficacy of GROs in Modulating Prostate Cancer Growth and Metastasis In vivo The efficacy in nude mice models is tested. Mice are inoculated s. c. with DU145 cells under mild anesthesia. After the establishment of palpable xenografts, mice are treated (six mice per group) with GR029A, control oligonucleotide (5'-GACTGTACCGAGGTGCAAG TACTCTA, with 3'amino modification), or PBS using the optimal administration route described above. Three treatment groups receive 0.5, 5 or 50 mg/kg doses twice per week for two weeks. Body weight and tumor size (measured with calipers) are monitored. At an appropriate time, the mice are euthanized by inhalation of $CO_2$ and tumors excised. Sections of the tumor are examined by morphological analysis and immunostaining, including nucleolin, PCNA, Ki 67 and TUNEL analysis for apoptosis. Similar experiments using the optimal (or economically feasible) dose are conducted to determine efficacy of GR029A in modulating PC-3 and LNCaP xenografts. Models of metastatic prostate cancer are then implemented.

Animals (fifteen per group) are implanted with tumors as described previously (Isaacs et al. (1978) Cancer Res. 38 (11 Pt 2): 4353-9; Zaccheo et al. (1998) Prostate 35 (4): 237-42), and treatment with GR029A begins about six weeks after implantation (or at the first appearance of palpable tumors in the rat model), and continued twice per week for a further six weeks. At this time (or before, if animals appear moribund or distressed), animals are euthanized and subjected to autopsy to examine primary tumor size and metastasis. Tumors and metastases are histologically examined as above.

Evaluation of Combination GRO-Cytotoxic Drug Therapies for Prostate Cancer

The efficacy of combination treatments of GR029A with chemotherapy drugs and other agents expected to affect growth-arrested cells were determined. Exemplary agents were selected from the following: mitoxantrone, etoposide, cis-platin, camptothecin, 5-fluorouracil, vinblastine, mithramycin A, dexamethasone, and caffeine (promotes progression through S phase cell cycle checkpoints). This group comprised agents with diverse mechanisms of action, e. g. topoisomerase I and II modulators, mitosis modulators, and DNA damaging agents. The activity of these was tested in cultured cells using the MTT assay to determine cell number. Cells were treated by addition of drug (at the GI3o dose) to the medium, followed 24 hours later by addition of GR029A (GI3o dose), or in the reverse sequence. For combinations for which there is synergistic activity, cells were examined for cell cycle perturbation (by flow cytometry) and apoptosis (flow cytometry of annexin V-stained cells). Synergistic combinations ae also tested in vivo, as described above.

Development of Homology Models of Nucleolin and Carrying Out of a "Virtual Screen" of a Library of Small Molecules to Identify Potential Nucleolin Modulators Small molecule modulators of nucleolin may be more practical alternatives to oligonucleotides. Homology modeling (with MSI Modeller and Homology programs) is used to build a 3D model of nucleolin from its sequence alignment with known structures of related proteins (16 have been identified). Standard techniques of backbone building, loop modeling, structural overlay and statistical analysis of the resulting models are used. The homology model will be refined using molecular dynamics.

The virtual screen uses the MSI Ludi software combined with the ACD database. Ludi fits molecules into the active site of nucleolin by matching complementary polar and hydrophobic groups. An empirical scoring function is used to prioritize the hits. Ludi also suggests modifications that may increase the binding affinity between the active oligonucleotides and nucleolin, and can also improve the homology model of nucleolin by inference from the binding of the active oligonucleotides. The ACD structural database contains 65,800 commercially and synthetically available chemicals that can be acquired immediately for further development. A selection of the most promising compounds is tested for protein binding and antiproliferative activity in cultured cells and in vivo.

Growth Modulatory Effects of G-Rich Oligonucleotides

The effects of four G-rich phosphodiester oligonucleotides (GROs) on the growth of tumor cells in culture were tested. These oligonucleotides consisted entirely of deoxyguanosine and thymidine and contained at least two contiguous guanosines. For increased stability to serum nucleases, oligonucleotides were modified at the 3'-terminus with a propylamino group. This modification protects the oligonucleotides from degradation in serum containing medium for at least twenty-four hours.

FIG. 1A-D shows the results of MTT assays for determining relative numbers of viable cells in treated cell lines derived from prostate (DU145), breast (MDA-MB-231, MCF-7) or cervical (HeLa) carcinomas.

Two oligonucleotides, GRO29A and GRO15A, consistently modulateed proliferation in all of the cell lines tested. For three of the cell lines, GRO29A had a more potent modulatory effect than GRO15A (for MCF-7 cells, the oligonucleotides had similar effects). The growth of cells treated with two other oligonucleotides, GRO15B and GR026A, was similar to that of the control water-treated cells (GR026A had a weak growth modulatory effect in MDA-MB-231 and HeLa cells).

Figure 1A:
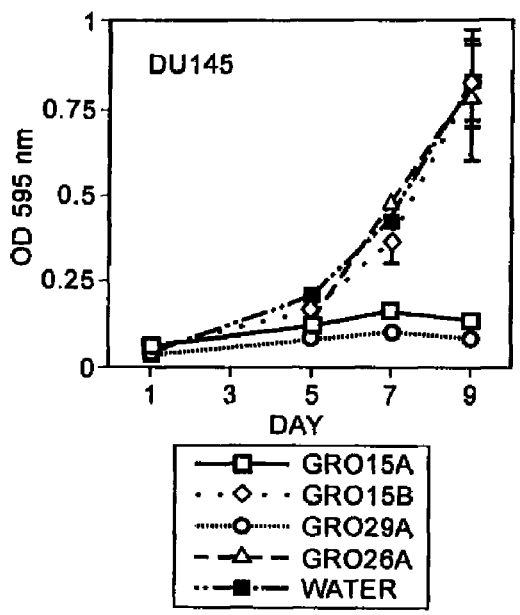
FIG. 1: MTT assays showing the growth of tumor cells treated with G-rich oligonucleotides or water as a control over time, wherein (A) the cell type is DU145, (B) the cell type is MDA-MB-231, (C) the cell type is HeLa, and (D) the cell type is MCF-7 and wherein D GRO15A, 0 GRO15B, 0 GRO29A, A GRO26A, and ES water.
Figure 1B:
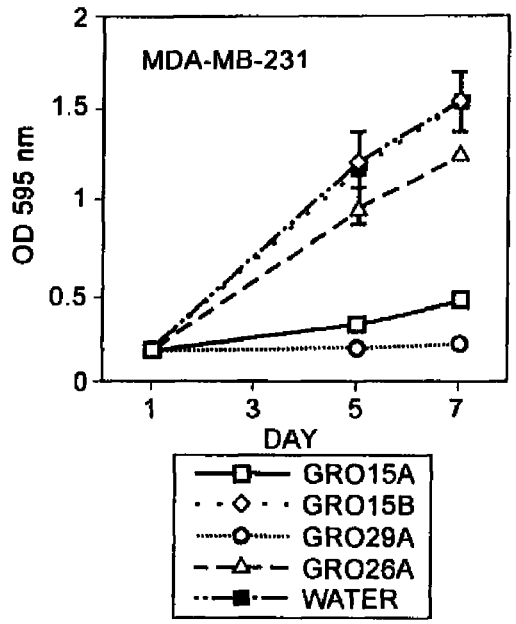
Figure 1C:
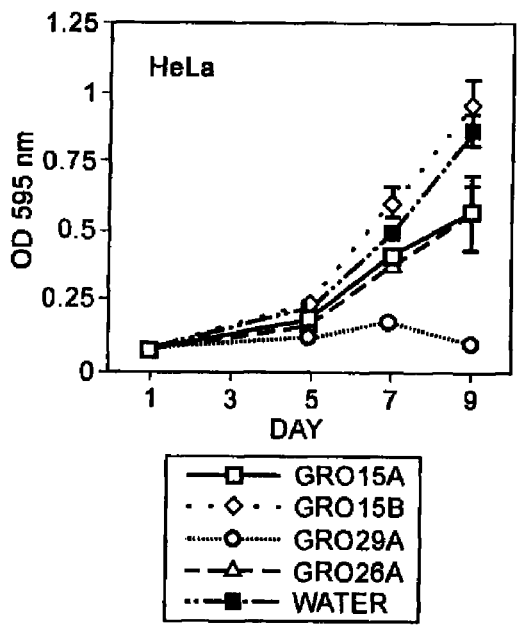
Figure 1D:
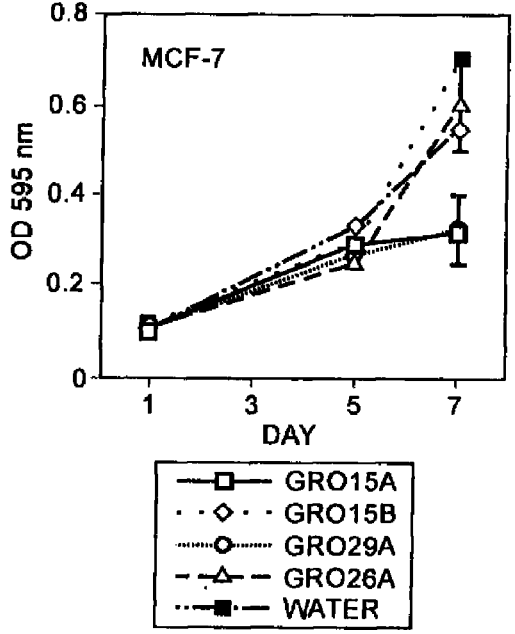
Figure 2A:
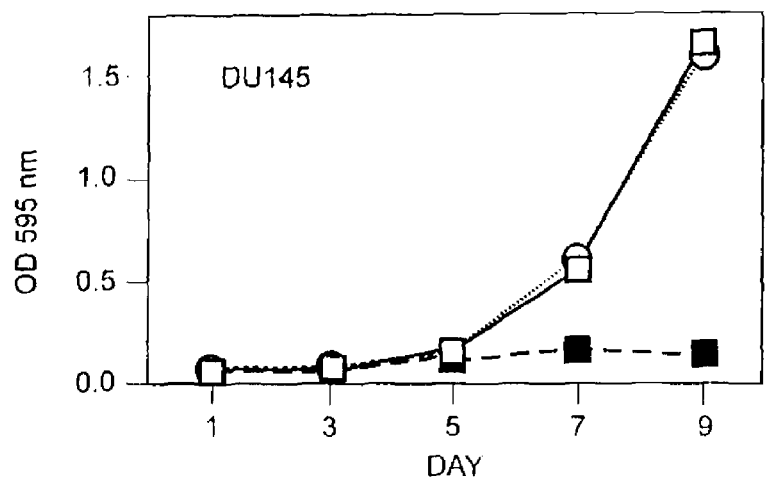
FIG. 2 illustrates the results of MTT assays showing the growth of (A) DU145 cells, (B) MDA-MB-231 cells, and (C) HS27 cells treated with GRO29A active oligonucleotide (closed squares), GRO15B (inactive oligonucleotide, half-filled squares), or no oligonucleotide (open squares).
Figure 2B:
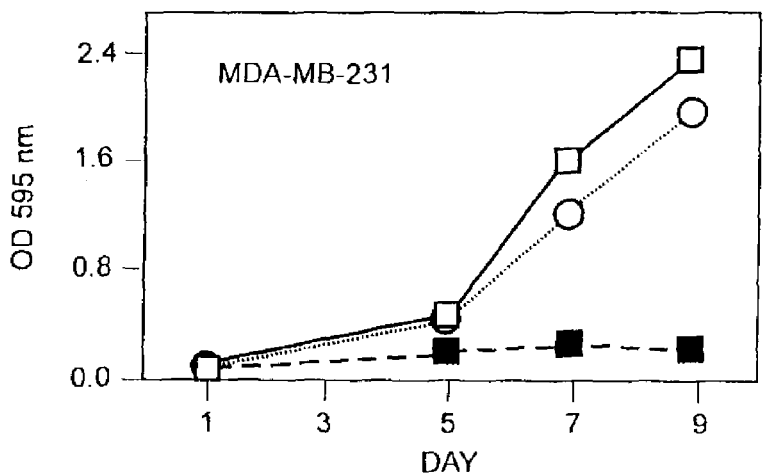
Figure 2C:
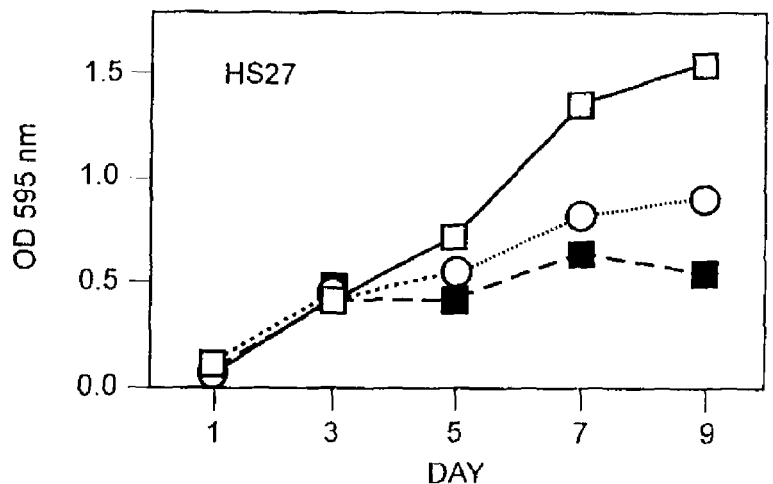

The results illustrated in FIG. 2A-C show that GRO29A has a lesser growth modulatory effect on a non-malignant cell line (HS27) compared to most malignant cell lines, for example, DU145, MDA-MG-231. Also, GRO29A has antiproliferative effects against leukemia cell lines, for example, K562 and U937, as shown in FIG. 3. It has a lesser growth modulatory effect against a non-malignant hematopoietic stem cell line (ATCC 2037).

G-Quartet Formation by G-Rich Oligonucleotides

To investigate the formation of G-quartet structures by the G-rich oligonucleotides, a U. V. melting technique described by Mergny et al. (1998) FEBS Lett. 435, 74-78 was used. This method relies on the fact that dissociation of G-quartets leads to a decrease in absorbance at 295 nm and is reported to give a more reliable indication of intramolecular G-quartet formation than measurement at 260 nm.

Figure 4A:
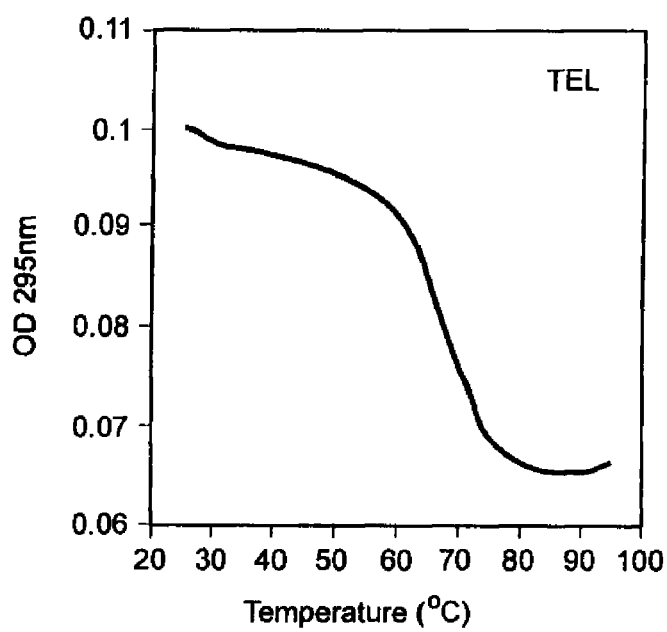
FIG. 4 are U. V. thermal renaturation curves to assess G-quartet formation by G-rich oligonucleotides wherein (A) TEL, (B) GR029A, (C) GR015A, (D) GRO1SG, and (E) GR026A.
Figure 4B:
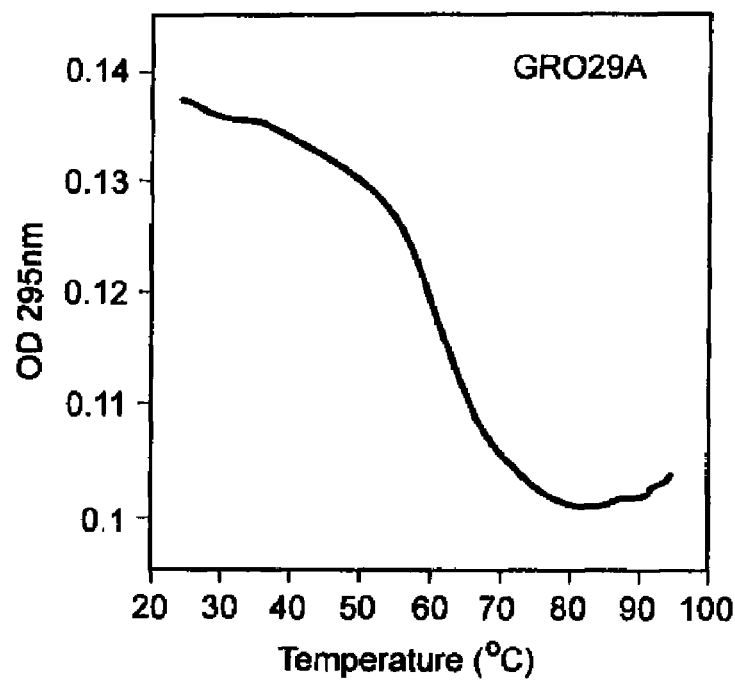
Figure 4C:
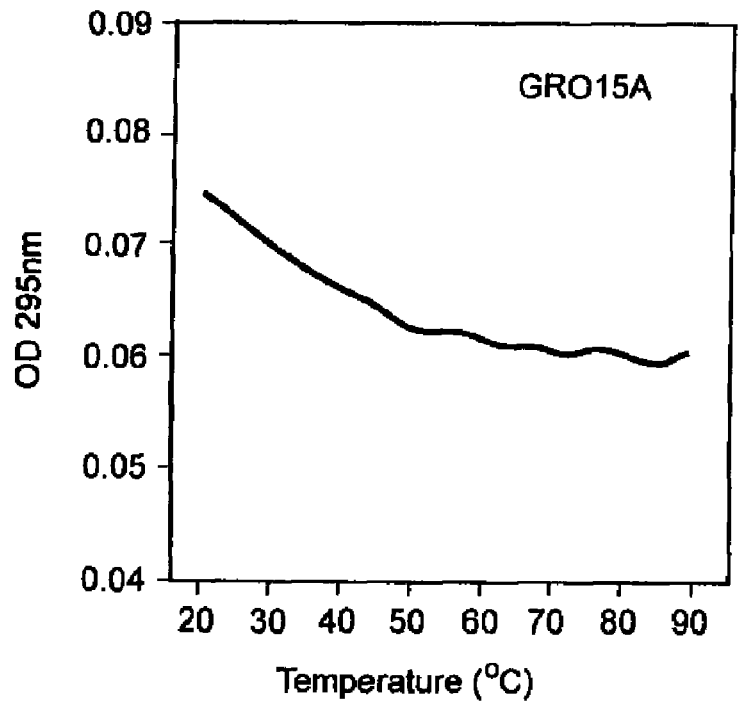
Figure 4D:
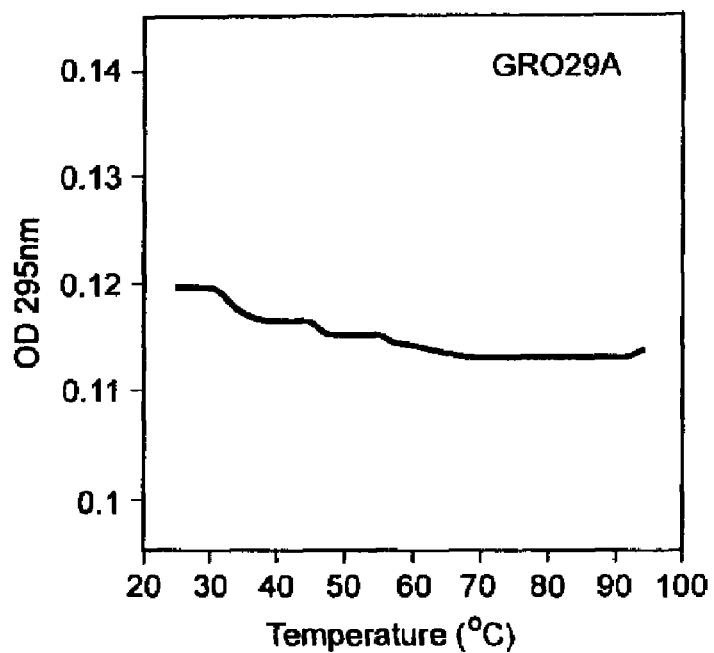
Figure 4E:
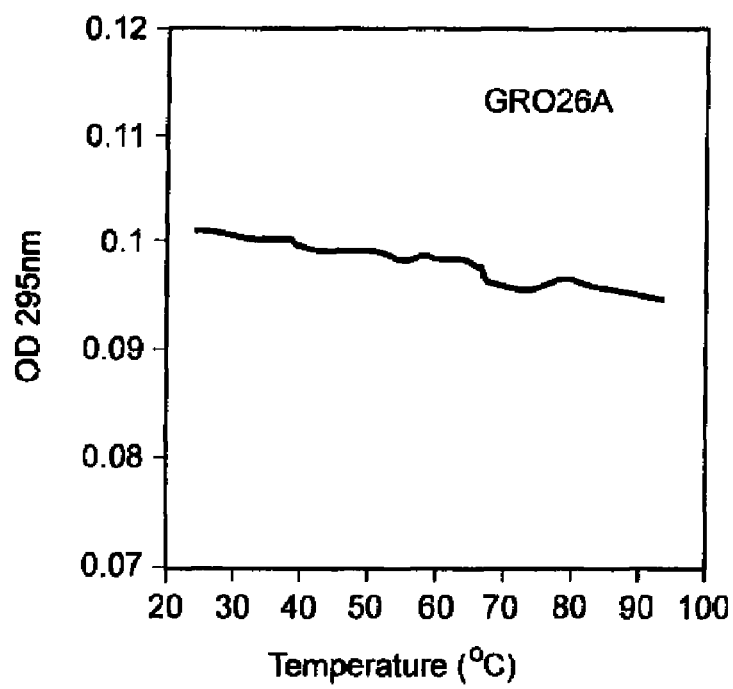

As a control for G-quartet formation, we used a singlestranded oligonucleotide, TEL. This oligonucleotide contains four repeats of the human telomere sequence 5'-TTAGGG and is known to form a G-quartet structure in vitro. Wang el al. (1993) Structure 1, 263-282. FIG. 4A shows the annealing curve for this sequence. G-quartet formation is indicated by a clear transition with a melting temperature of 66° C. The transition was reversible and a slight hysteresis was observed between heating and cooling curves (not shown) at 0.5° C./min indicating a fairly slow transition. The most active oligonucleotide, GRO29A (FIG. 4B), showed a similar profile, clearly indicating the presence of G-quartets. The slightly less active oligonucleotide, GRO15A (FIG. 4C), showed a decrease in absorbance between 20 and 50° C. This is suggestive of G-quartet formation, but a clear transition is not seen since the melting temperature is lower than for TEL (FIG. 4A) or GRO15A (FIG. 4C). The curves for the two inactive oligonucleotides, GRO15B (FIG. 4B) and GR026A (FIG. 4E), showed no transition characteristic of intramolecular G-quartet formation under these conditions.

Active G-Rich Oligonucleotides Bind to a Specific Cellular Protein.

To investigate further the mechanism of the growth modulatory effects, binding of the oligonucleotides to cellular proteins was examined. 5'-Radiolabeled oligonucleotides were incubated with HeLa nuclear extracts, alone or in the presence of unlabeled competitor oligonucleotide, and examined by an electrophoretic mobility shift assay. The G-quartet forming telomere sequence oligonucleotide, TEL, was included as a competitor in this experiment. A single stranded oligonucleotide, TEL, was also included as a competitor in this experiment. TEL contains four repeats of the human telomere sequence 5'-TTAGGG-3', and is known to form a G-quartet structure in vitro. Wang et al. (1993) Structure 1, 263-282. FIG. 6A shows the formation of a stable proteinoligonucleotide complex (marked "*"). This band was intense when the labeled oligonucleotide was one of the growth modulatory oligonucleotides, GRO15A or GRO29A (lanes 1 and 5), but the inactive oligonucleotide, GR026A, formed only a weak complex (lane 9).

To further confirm that the same protein is binding to TEL and to the growth modulatory oligonucleotides, a similar experiment was carried out in which TEL was labeled. Labeled TEL formed two complexes with nuclear extracts in the absence of competitor oligonucleotides (bands A and B, FIG. 6B). The slower migrating TEL-protein complex (band A) was competed for by unlabeled growth modulatory oligonucleotides (GRO15A, GRO29A) but not inactive oligonucleotides (GR026A, GRO15B). The faster migrating complex (band B) was specific for TEL and was not competed for by G-rich oligonucleotides. Hence binding of competitor GROs was characterized by a decrease in the intensity of band A and an increase in the intensity of band B (due to release of labeled TEL from band A complex). This assay allowed comparison of the binding affinity of native GROs (without 5'-phosphorylation) and was used for assessment of protein binding in subsequent experiments. To ensure that competition was due to binding of the GRO to the protein component of complex A, and not a result of interaction between GRO and TEL oligonucleotide, a mobility shift on a 15% polyacrylamide gel was carried out. No shifted bands were observed when labeled TEL was incubated with GROs in the absence of protein (data not shown).

To determine the approximate molecular weight of the protein involved in complex A, and to confirm that competition for this complex results from direct binding of the protein to oligonucleotides, a UV cross-linking study was conducted. 5'-Labeled oligonucleotides and HeLa nuclear extracts were incubated alone or in the presence of unlabeled competitor oligonucleotides.

Figure 6C:

The samples were then irradiated with UV light resulting in cross-link formation between protein residues and thymidines in the oligonucleotide. The protein was thus radiolabeled and could be detected on a SDS-polyacrylamide gel. FIG. 6C shows the results of this experiment. Both TEL and GRO15A crosslinked to a protein (marked "*") which was competed for by antiproliferative oligonucleotides and TEL, but not by inactive GR026A. The most active oligonucleotide, GR029A, also formed this approximately 100 kDa complex and another complex of higher molecular weight (not shown).

Inactive GR026A produced a barely visible band at approximately 100 kDa (not shown).

Figure 6D:
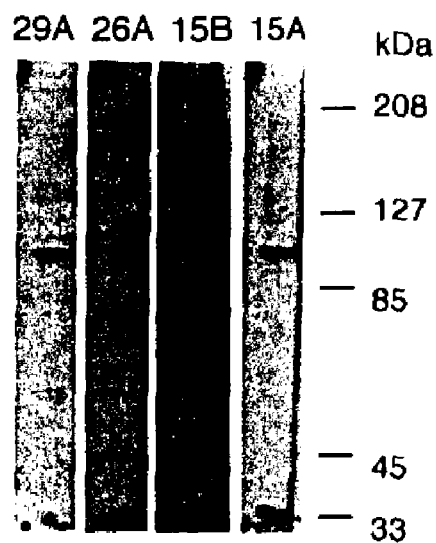

The molecular weight of the nuclear protein was more accurately determined by Southwestern blotting. HeLa nuclear extracts were electrophoresed on an 8% polyacrylamide-SDS gel and transferred to a PVDF membrane. The membrane was blocked and cut into strips. Each strip was incubated at 4° C. with a 32P-labeled G-rich oligonucleotide in the presence of unrelated unlabeled double stranded and single stranded DNA to block non-specific binding. FIG. 6D shows active oligonucleotides GRO15A and GR029A hybridized to a single protein band at 106 kDa (the band was exactly adjacent to a 106 kDa molecular mass marker, not shown). Inactive oligonucleotides GRO15B and GR026A hybridized only weakly to this protein. The data presented in FIG. 6 shows correlation between activity and protein binding. These experiments also demonstrate that binding of GROs to p106 is highly specific, since only a single protein band is recognized with high affinity (see FIG. 6D). This was not simply a result of hybridization to an abundant protein, as India ink staining of immobilized nuclear extracts showed the presence of many other protein bands which were equally or more intense than the band at 106 kDa (data not shown).

Antiproliferative Activity Correlates with Protein Binding

Figure 7D:
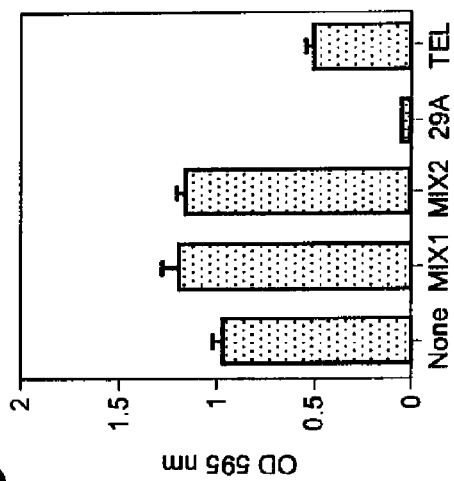

To further confirm the relationship between activity and binding to the 106 kDa protein, four more G-rich oligonucleotides were synthesized and their effects were compared with active (GR029A) and inactive (GRO15B) oligonucleotides. FIGS. 7A and 7B show that the growth modulatory effect of the oligonucleotides correlated with their ability to compete for the TEL-binding protein. Three of the new oligonucleotides (GRO14A, GR025A, GR028A) displayed a moderate antiproliferative activity but were not as potent as GR029A. Oligonucleotide GRO14B showed no antiproliferative activity. Correspondingly, the moderate active oligonucleotides were able to compete with TEL for binding to the nuclear protein, though not as effectively as GR029A. The non-modulatory oligonucleotide, GRO14B, was unable to compete for protein binding.

Figure 8:
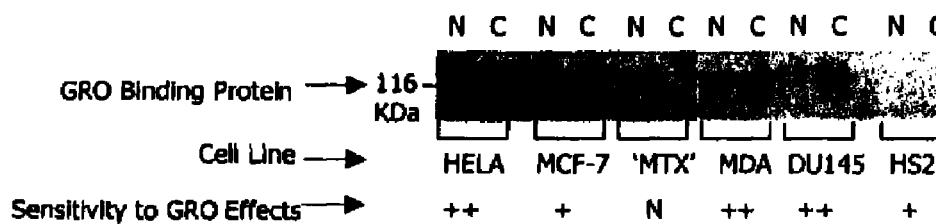
FIG. 8: (Top) Southwestern blot using radiolabeled GRO15A to detect GRO binding protein in nuclear (N) and cytoplasmic (C) extracts from various cell lines. (Bottom): Sensitivity of various cell lines to the growth modulatory effects of GRO29A and GRO15A.

The importance of the approximately 106 kDa protein in GRO effects was further demonstrated by the correlation between the sensitivity of various cell lines to the GRO-induced antiproliferative effects and levels of this protein in nuclear and cytoplasmic extracts from these cell lines, as shown in FIG. 8.

Effects of Non-G-rich Oligonucleotides. To investigate the specificity of the antiproliferative effects, the growth modulatory effects of non-G-rich oligonucleotides and heparin, a polyanionic polysaccharide, were examined.

Figure 7C:
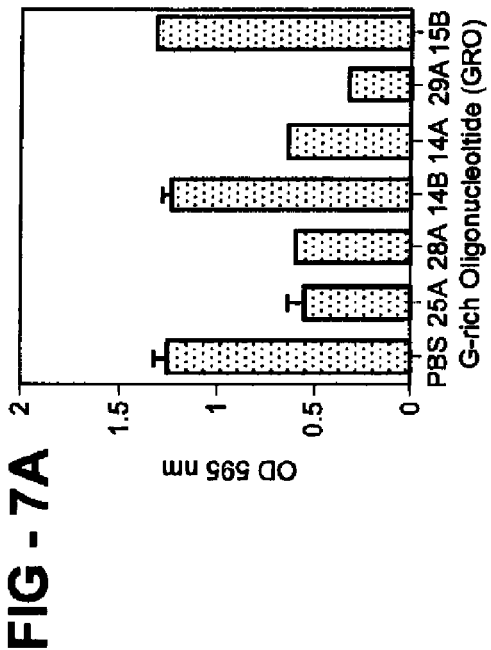
Figure 7B:
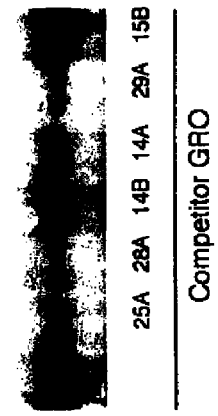

FIG. 7C shows that at 10 uM concentration (equivalent to approximately 0.1 mg/ml for GR029A), neither a 3'-modified C-rich oligonucleotide (CRO) nor a 3'-modified mixed base oligonucleotide (MIX1) were able to modulate the growth of MDA-MB-231 breast cancer cells. This result showed that the growth modulating activity of GRO15A and GR029A was not simply nonspecific effects resulting from the presence of 3'-modified oligonucleotide but rather relied on some unique feature of these sequences. Heparin also had no effect on cell growth when added to the culture medium at a concentration of 20 units/ml (approximately 0.12 mg/ml), further demonstrating that the antiproliferative effects of active oligonucleotides are not simply a result of their polyanionic character.

To examine the antiproliferative properties of non-3'-proteted oligonucleotides, a slightly modified treatment protocol was used in which oligonucleotides were added to cells in serum-free medium (see "Experimental Procedures"). FIG. 7D shows that similar effects could also be seen with unmodified oligonucleotides under these conditions. Both 29A-OH (a 3'-unmodified analog of GR029A) and TEL modulateed the growth of cells, whereas two mixed sequence oligonucleotides had no growth modulatory effects.

The protein binding properties of these non-G-rich oligonucleotides and heparin (not shown) were also compared. As expected, the unlabeled growth modulatory oligonucleotides GR029A, 29A-OH, and TEL competed strongly for protein binding in the competitive electrophoretic mobility shift assay (using labeled TEL oligonucleotide and MDA-MB-231 nuclear extracts) at 10 nM concentration (approximately 0.1 pg/ml for GR029A). In accord with its lesser antiproliferative activity, TEL competed slightly less effectively than 29A-OH or GR029A. No competition was observed using 10 nM unlabeled CRO, MIX2, or MIX3 or in the presence of 0.02 units/ml heparin (approximately 0.12 ug/ml). However, the mixed sequence oligonucleotide, MIX1, was anomalous. Although this oligonucleotide had no effect on the growth of cells, it appeared to compete for protein binding in the competitive EMSA.

Clinical Trial/Phase I Study

SEQ ID NO: 12, a G-rich oligonucleotide (GRO) aptamer comprising a single-strand oligonucleotide of 26 bases, was selected for the study. Common to other aptamers of the invention described herein, the SEQ ID NO: 12 aptamer self-anneals to form a bimolecular quadruplex structure that is extremely stable and resistant to degradation by serum enzymes. Characterization of the aptamer demonstrates its specificity for nucleolin, which is expressed on the cell surface in tumors. In-vitro experiments involving SEQ ID NO:12 demonstrated that nucleolin-binding leads to internalization of the SEQ ID NO:12 aptamer-nucleolin complex and a strong anti-proliferative response in tumor cells, i.e. strong ability to modulate tumor cell proliferation. Preclinical data indicates potential of SEQ ID NO: 12 against a wide variety of solid and hematologic malignancies.

A Phase I, open label, non-randomized dose escalation study of SEQ ID NO:12 was conducted on 17 human individuals with various advanced malignancies. These subjects were men and women aged 18 years or older with histologically/cytologically confirmed solid tumors that were metastatic or unresectable and for which standard curative measures did not exist or were no longer effective, or that was refractory or recurrent after conventional treatment. After these 17 individuals had received treatment, only individuals with RCC (renal-cell carcinoma) or non-small-cell lung cancer (NSCLC) were enrolled in the clinical trial to obtain data for more homogenous patient populations and thereby enhance the quality of the results.

Following these findings, the trial was extended to include additional individuals ("patients") with RCC (renal-cell carcinoma) or non-small-cell lung cancer. All of said individuals had progressive, metastatic cancers upon entry to the study. It should be noted that none of the individuals had received chemotherapy, radiotherapy or any investigational agent for cancer within the 4 weeks prior to entry to the study or 6 weeks prior for nitrosourea or mitomycin C. All individuals enrolled in the study were evaluable for toxicity and response and had measurable disease, i.e. able to be measured accurately in one or more dimension(s). Participants of the study were recruited at one site: the University of Louisville, James Brown Cancer Center, in Louisville, Ky., USA. The study was conducted in accordance with Good Clinical Practices and the Declaration of Helsinki. Institutional Review Board approval and informed patient consent were obtained before the study began.

Study Design

The SEQ ID NO:12 aptamer was administered to individuals as a continuous intravenous infusion. All individuals received one or two cycles of treatment. The dose escalation protocol provided a division of the subjects into cohorts of 3 in sequential order. If no individuals in a cohort experienced DLT within 28 days of treatment, the dosage was escalated to the next level. The dosage was increased up to 10 mg/kg/day for 7 days in the first 17 individuals and increased up to 40 mg/kg/day for 7 days in the RCC/NSCLC extension. The original starting dose was about 1 mg/kg/day for 4 days for both sets of individuals.

If no subject in the first cohort experienced DLT within 14 days of treatment, the dose for the next cohort was escalated to the next level. The starting dose in the protocol was 1 mg/kg/day, which was incrementally increased as described above to a maximum dose of 40 mg/kg/day. For this study, DLT was identified as grade 3-4 non-hematological toxicity, grade 4 hematological toxicity that persisted for 3 or more days, grade 4 febrile neutropenia, or grade 4 thrombocytopenia with bleeding. Toxicity was graded according to the National Cancer Institute Common Terminology for Adverse Events ("NCI-CTCAE") version 3.0.

Dose escalation was accomplished by doubling until a biological effect was noted (i.e., by development of NCI-CTCAE grade 2 toxicity), at which point the dose was escalated using a modified Fibonacci design (dose increments to 1.6 times the pervious dose level). The maximum dose for the study was 40 mg/kg/day.

Assessments

Baseline evaluations included medical history, 12-lead electrocardiogram, safety assessments and tumor measurements within 1 week of the start of the study. Individuals were monitored in the hospital during infusion of the SEQ ID NO:12 aptamer (days 1-8) and then evaluated subsequently on days 15, 29 and 58.

Efficacy was assessed by tumor measurements and radiological evaluation at baseline (4 or more weeks prior to the start of the study), at day 29 and day 58.

Tumor measurements were conducted using photographs (skin lesions), chest X-rays, CT scans, magnetic resonance imaging (MRI) and ultrasound. The assessments of tumor measurements were conducted using the Response Evaluation Criteria in Solid Tumors (RECIST) guidelines. See Arbuck et al., (2000) *Journal Nat'l Cancer Inst.*, 92: 205-16. All tumor measurements were taken in metric notation using a ruler or caliper.

Plasma samples for pharmokinetic analysis were taken at regular intervals during and after infusion (up to 24 hours post-infusion). Full 24-hour urine collections were taken on each day of infusion and on the day after infusion. Plasma and urine samples were also collected on days 15 and 29.

Results

As a preliminary note, tumor response was evaluated using RECIST guidelines and categorized as complete response (CR), partial response (PR), stable disease (SD) or progressive disease (PD). Changes in only the largest diameter (unidimensional measurement) of tumor lesions were evaluated using RECIST. See Therasse et al. (2000) *J Natl Cancer Inst* 92:205-16. Response was confirmed by repeat assessments 4 weeks after criteria for response were first met. For confirmation of SD, follow-up measurements were required to meet SD criteria at least once after study entry at a minimum interval of 4 weeks.

Doses up to 40 mg/kg/day for up to 7 days were well tolerated with no serious toxicity of any type related to drug administration observed in the study. A response rate of 17% and clinical benefit of 75% in patients in advanced, metastatic RCC were observed while 40% of NSCLC patients had stable disease for the duration of the study.

More specifically, 8.4% of RCC subjects had a complete response, 8.4% had a partial response, and 58% had stable disease for the duration of the study. The overall response rate (CR+PR) was 17%, and clinical benefit (CR+PR+SD) was 75%.

Case Reports for Two RCC Responders

One RCC responder showed no evidence of disease 26 months after receiving one seven-day infusion of the SEQ ID NO:12 aptamer at a 10 mg/kg dose. This responder did develop a single brain metastasis 18 months after treatment with the modified oligonucleotide aptamer. The brain metastasis was treated with surgical resection followed by whole-brain radiotherapy.

The second RCC responder showed a decrease in the sum of greatest linear dimensions of target lesions of about 70% from baseline. This patient received two seven-day infusions of the modified oligonucleotide aptamer at a 22 mg/kg dose.

Any patents or publications mentioned in this specification are indicative of the levels of those skilled in the art to which the invention pertains. These patents and publications are herein incorporated by reference to the same extent as if each individual publication was specifically designated as being incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated aptamer consisting of a nucleic acid sequence selected from SEQ ID NO: 1-4, 7-9, 11, 13-16, and 18.

2. A composition comprising the isolated aptamer of claim 1.

3. The composition of claim 2, wherein said aptamer is capable of binding to nucleolin.

4. The composition of claim 2, being capable of inhibiting nucleolin activity.

5. The composition of claim 2, being capable of modulating tumor cell proliferation.

6. The composition of claim 2, being capable of inducing apoptosis.

7. The composition of claim 2, wherein binding of the aptamer to cell surface nucleolin forms a complex and mediates internalization of the complex.

8. The composition of claim 7, wherein said binding interferes with nucleolin function in the nucleus, cytoplasm, or membrane.

9. The composition of claim 5, wherein the cell proliferation is neoplastic or dysplastic growth.

10. The composition of claim 5, wherein the cell proliferation is that of lymphoma, leukemia, renal carcinoma, sarcoma, hemangiopericytoma, melanoma, abdominal cancer, gastric cancer, colon cancer, cervical cancer, prostate cancer, pancreatic cancer, breast cancer, or non-small cell lung cancer.

11. The composition of claim 10, wherein the cell proliferation is that of leukemia or renal carcinoma.

* * * * *

SEQUENCE LISTING

<160> NUMBER OF SEQ ID NOS: 21

<210> SEQ ID NO 1
<211> LENGTH: 14
<212> TYPE: DNA
<213> ORGANISM: Artificial Sequence
<220> FEATURE:
<223> OTHER INFORMATION: GRO14A

```
<400> SEQUENCE: 1
gttgtttggg gtgg                                                14

<210> SEQ ID NO 2
<211> LENGTH: 15
<212> TYPE: DNA
<213> ORGANISM: Artificial Sequence
<220> FEATURE:
<223> OTHER INFORMATION: GRO15A

<400> SEQUENCE: 2
gttgtttggg gtggt                                               15

<210> SEQ ID NO 3
<211> LENGTH: 25
<212> TYPE: DNA
<213> ORGANISM: Artificial Sequence
<220> FEATURE:
<223> OTHER INFORMATION: GRO25A

<400> SEQUENCE: 3
ggttggggtg ggtggggtgg gtggg                                    25

<210> SEQ ID NO 4
<211> LENGTH: 28
<212> TYPE: DNA
<213> ORGANISM: Artificial Sequence
<220> FEATURE:
<223> OTHER INFORMATION: GRO28A

<400> SEQUENCE: 4
tttggtggtg gtggttgtgg tggtggtg                                 28

<210> SEQ ID NO 5
<211> LENGTH: 29
<212> TYPE: DNA
<213> ORGANISM: Artificial Sequence
<220> FEATURE:
<223> OTHER INFORMATION: GRO29A

<400> SEQUENCE: 5
tttggtggtg gtggttgtgg tggtggtgg                                29

<210> SEQ ID NO 6
<211> LENGTH: 29
<212> TYPE: DNA
<213> ORGANISM: Artificial Sequence
<220> FEATURE:
<223> OTHER INFORMATION: GRO29-2

<400> SEQUENCE: 6
tttggtggtg gtggttttgg tggtggtgg                                29

<210> SEQ ID NO 7
<211> LENGTH: 29
<212> TYPE: DNA
<213> ORGANISM: Artificial Sequence
<220> FEATURE:
<223> OTHER INFORMATION: GRO29-3

<400> SEQUENCE: 7
tttggtggtg gtggtggtgg tggtggtgg                                29

<210> SEQ ID NO 8
<211> LENGTH: 29
<212> TYPE: DNA
```

```
<213> ORGANISM: Artificial Sequence
<220> FEATURE:
<223> OTHER INFORMATION: GRO29-5

<400> SEQUENCE: 8
tttggtggtg gtggtttggg tggtggtgg                                    29

<210> SEQ ID NO 9
<211> LENGTH: 13
<212> TYPE: DNA
<213> ORGANISM: Artificial Sequence
<220> FEATURE:
<223> OTHER INFORMATION: GRO29-13

<400> SEQUENCE: 9
tggtggtggt ggt                                                     13

<210> SEQ ID NO 10
<211> LENGTH: 11
<212> TYPE: DNA
<213> ORGANISM: Artificial Sequence
<220> FEATURE:
<223> OTHER INFORMATION: GRO11A

<400> SEQUENCE: 10
ggtggtggtg g                                                       11

<210> SEQ ID NO 11
<211> LENGTH: 14
<212> TYPE: DNA
<213> ORGANISM: Artificial Sequence
<220> FEATURE:
<223> OTHER INFORMATION: GRO14C

<400> SEQUENCE: 11
ggtggttgtg gtgg                                                    14

<210> SEQ ID NO 12
<211> LENGTH: 26
<212> TYPE: DNA
<213> ORGANISM: Artificial Sequence
<220> FEATURE:
<223> OTHER INFORMATION: GRO26B

<400> SEQUENCE: 12
ggtggtggtg gttgtggtgg tggtgg                                       26

<210> SEQ ID NO 13
<211> LENGTH: 56
<212> TYPE: DNA
<213> ORGANISM: Artificial Sequence
<220> FEATURE:
<223> OTHER INFORMATION: GRO56A

<400> SEQUENCE: 13
ggtggtggtg gttgtggtgg tgtggttgt ggtggtggtg gttgtggtgg tggtgg       56

<210> SEQ ID NO 14
<211> LENGTH: 32
<212> TYPE: DNA
<213> ORGANISM: Artificial Sequence
<220> FEATURE:
<223> OTHER INFORMATION: GRO32A

<400> SEQUENCE: 14
ggtggttgtg gtggttgtgg tggttgtggt gg                                32
```

```
<210> SEQ ID NO 15
<211> LENGTH: 32
<212> TYPE: DNA
<213> ORGANISM: Artificial Sequence
<220> FEATURE:
<223> OTHER INFORMATION: GRO32B

<400> SEQUENCE: 15
tttggtggtg gtggttgtgg tggtggtggt tt                                    32

<210> SEQ ID NO 16
<211> LENGTH: 29
<212> TYPE: DNA
<213> ORGANISM: Artificial Sequence
<220> FEATURE:
<223> OTHER INFORMATION: GRO29-6

<400> SEQUENCE: 16
ggtggtggtg gttgtggtgg tggtggttt                                        29

<210> SEQ ID NO 17
<211> LENGTH: 28
<212> TYPE: DNA
<213> ORGANISM: Artificial Sequence
<220> FEATURE:
<223> OTHER INFORMATION: GRO28B

<400> SEQUENCE: 17
tttggtggtg gtggtgtggt ggtggtgg                                         28

<210> SEQ ID NO 18
<211> LENGTH: 10
<212> TYPE: DNA
<213> ORGANISM: Artificial Sequence
<220> FEATURE:
<223> OTHER INFORMATION: GRO13A

<400> SEQUENCE: 18
tggtggtggt                                                             10

<210> SEQ ID NO 19
<211> LENGTH: 35
<212> TYPE: DNA
<213> ORGANISM: Artificial Sequence
<220> FEATURE:
<223> OTHER INFORMATION: mixed sequence 35-mer oligonucleotide

<400> SEQUENCE: 19
tcgagaaaaa ctctcctctc cttccttcct ctcca                                 35

<210> SEQ ID NO 20
<211> LENGTH: 24
<212> TYPE: DNA
<213> ORGANISM: Artificial Sequence
<220> FEATURE:
<223> OTHER INFORMATION: 5'- 32P-labeled TEL oligonucleotide

<400> SEQUENCE: 20
ttagggttag ggttagggtt aggg                                             24

<210> SEQ ID NO 21
<211> LENGTH: 26
<212> TYPE: DNA
```

```
<213> ORGANISM: Artificial Sequence
<220> FEATURE:
<223> OTHER INFORMATION: control oligonucleotide

<400> SEQUENCE: 21
gactgtaccg aggtgcaagt actcta                                              26
```